(12) United States Patent
Chang et al.

(10) Patent No.: US 6,908,966 B2
(45) Date of Patent: Jun. 21, 2005

(54) WATER-DISPERSIBLE, CATIONIC POLYMERS, A METHOD OF MAKING SAME AND ITEMS USING SAME

(75) Inventors: Yihua Chang, Portland, OR (US); Frederick J. Lang, Neenah, WI (US); Kenneth Y. Wang, Alpharetta, GA (US); Franklin M. Chen, Portland, OR (US); Kelly D. Branham, Winneconne, WI (US); Kim G. Schick, Menasha, WI (US); Walter T. Schultz, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/814,403

(22) Filed: Mar. 22, 2001

(65) Prior Publication Data

US 2003/0045645 A1 Mar. 6, 2003

(51) Int. Cl.[7] .............................................. C08L 33/00
(52) U.S. Cl. ...................................... 525/217; 525/218
(58) Field of Search ................................. 525/217, 218

(56) References Cited

U.S. PATENT DOCUMENTS

| | | | |
|---|---|---|---|
| 2,185,789 A | 1/1940 | Jacque | |
| 2,265,913 A | 12/1941 | Lilienfeld | |
| 2,306,451 A | 12/1942 | Lilienfeld | |
| 2,831,852 A | 4/1958 | Savage | |
| 2,892,822 A | * 6/1959 | Gray et al. .................. | 528/39 |
| 3,097,991 A | 7/1963 | Miller et al. | |
| 3,099,067 A | 7/1963 | Merriam et al. | |
| RE25,880 E | 10/1965 | Cline | |
| 3,255,140 A | 6/1966 | Sinn | |
| 3,255,141 A | 6/1966 | Damm | |
| 3,340,327 A | 9/1967 | Spellberg | |
| 3,388,082 A | 6/1968 | Rodgers | |
| 3,406,688 A | 10/1968 | Cubitt | |
| 3,435,705 A | 4/1969 | Harmon | |
| 3,453,261 A | 7/1969 | Scherff | |
| 3,461,193 A | 8/1969 | Gilardi | |
| 3,480,016 A | 11/1969 | Costanza et al. | |
| 3,483,240 A | 12/1969 | Boudreau | |
| 3,484,394 A | 12/1969 | Holdstock | |
| 3,498,913 A | 3/1970 | Sellet | |
| 3,515,325 A | 6/1970 | Kalwaites | |
| 3,521,638 A | 7/1970 | Parrish | |
| 3,546,755 A | 12/1970 | Lynch, Jr. | |
| 3,554,862 A | 1/1971 | Hervey | |
| 3,561,447 A | 2/1971 | Alexander | |
| 3,564,677 A | 2/1971 | Kalwaites | |
| 3,577,586 A | 5/1971 | Kalwaites et al. | |
| 3,582,519 A | 6/1971 | Gomsi | |
| 3,595,454 A | 7/1971 | Kalwaites | |
| 3,616,797 A | 11/1971 | Champaigne, Jr. et al. | |
| 3,632,507 A | 1/1972 | Witt | |

(Continued)

FOREIGN PATENT DOCUMENTS

| | | |
|---|---|---|
| BE | 748453 | 4/1970 |
| CA | 631395 | 11/1961 |
| CA | 2057692 | 10/1992 |
| DE | 1719395 | 12/1970 |
| EP | 0 100 370 A1 | 2/1984 |
| EP | 0 103 902 A1 | 3/1984 |
| EP | 0 303 528 B1 | 2/1989 |
| EP | 0 320 594 B2 | 6/1989 |
| EP | 0 416 427 | 3/1991 |

(Continued)

OTHER PUBLICATIONS

Abstract Derwent WPI and JAPIO, JP 03–239709 (Lion Corp) Oct. 25, 1991.
Carlsson et al., "Thermal Gelation of Nonionic Cellulose Ethers and Ionic Surfactants in Water", *Colloids and Surfaces*, vol. 47, pp. 147–165 (1990).
Abstract Derwent WPI, J: 1–306661 (Lion Corp) Dec. 11, 1989.
Chowdhury et al., "Direct Observation of the Gelatin of Rodlike Polymers", *Poly. Mat. Sci. and Eng.*, vol. 59, pp. 1045–1052 (9/88).
Abstract Derwent WPI and JAPIO, JP 63/139906 (Lion Corp.) Jun. 11, 1988.
Nagura et al., "Temperature–Viscosity Relationships of Aqueous Solutions of Cellulose Ethers", Kobunshi Ronbunshu, vol. 38 (3), pp. 133–137 (8/80).
Stafford et al., "Temperature Dependence of the Disintegration times of compressed tablets containing hydroxypropylcellulose as binder", *J. Pharm. Pharmac.*, vol. 30, pp. 1–5 (8/77).
Govindan, T.S., "Process for Making Smooth Vapro–Permeable Microporous Sheet Material", *Defensive Publication*, vol. T901 (007), (8/72).
Kohlhammer, *Nonwovens Report International*, vol. 342, pp. 20–22, 28–31 (9/99).
*Soap & Cosmetics*, vol. 76(3), p. 12 (Mar. 2000).
Patent Abstract Japan, JP 06–207324 (Unitka Ltd.), Jul. 26, 1994.
D 5034–11, "Standard Test Method for Breaking Force and Elongation of Textile Fabrics (Grab Test)," 1994 Ann. Book of ASTM Standards, vol. 7.02, pp. 708–709 (1994).
Abstract Derwent WPI, JP 5–179548 (Lion Corp), Jul. 20, 1993).

*Primary Examiner*—Bernard Lipman
(74) *Attorney, Agent, or Firm*—Brinks Hofer Gilson & Lione

(57) ABSTRACT

The present invention is directed to triggerable, water-dispersible cationic polymers. The present invention is also directed to a method of making triggerable, water-dispersible cationic polymers and their applicability as binder compositions. The present invention is further directed to fiber-containing fabrics and webs comprising triggerable, water-dispersible binder compositions and their applicability in water-dispersible personal care products, such as wet wipes.

10 Claims, No Drawings

U.S. PATENT DOCUMENTS

| | | |
|---|---|---|
| 3,639,199 A | 2/1972 | Brandts et al. |
| 3,654,064 A | 4/1972 | Laumann |
| 3,656,672 A | 4/1972 | Kalwaites |
| 3,663,348 A | 5/1972 | Liloi et al. |
| 3,665,923 A | 5/1972 | Champaigne, Jr. |
| 3,670,069 A | 6/1972 | Mitchell et al. |
| 3,670,731 A | 6/1972 | Harron |
| 3,683,919 A | 8/1972 | Ells |
| 3,702,610 A | 11/1972 | Sheppard et al. |
| 3,709,876 A | 1/1973 | Glomski |
| 3,712,847 A | 1/1973 | Rasmussen |
| 3,719,540 A | 3/1973 | Hall |
| 3,753,826 A | 8/1973 | Plummer |
| 3,766,002 A | 10/1973 | Greif et al. |
| 3,800,797 A | 4/1974 | Tunc |
| 3,804,092 A | 4/1974 | Tunc |
| 3,838,695 A | 10/1974 | Comerford et al. |
| 3,839,319 A | 10/1974 | Greminger |
| 3,859,125 A | 1/1975 | Miller et al. |
| 3,865,918 A | 2/1975 | Mitchell et al. |
| 3,867,324 A | 2/1975 | Clendinning |
| 3,867,549 A | 2/1975 | Costello et al. |
| 3,869,310 A | 3/1975 | Fukushima et al. |
| 3,881,210 A | 5/1975 | Drach et al. |
| 3,881,487 A | 5/1975 | Schrading |
| 3,882,869 A | 5/1975 | Hanke |
| 3,897,782 A | 8/1975 | Tunc |
| 3,911,917 A | 10/1975 | Hanke |
| 3,913,579 A | 10/1975 | Srinivasan et al. |
| 3,923,592 A | 12/1975 | George et al. |
| 3,926,951 A | 12/1975 | Lindenfors et al. |
| 3,939,836 A | 2/1976 | Tunc |
| 3,950,578 A | 4/1976 | Laumann |
| 3,952,745 A | 4/1976 | Duncan |
| 3,959,569 A | 5/1976 | Burkholder, Jr. |
| 3,976,734 A | 8/1976 | Dunning et al. |
| 3,978,257 A | 8/1976 | Ring |
| RE28,957 E | 9/1976 | Drelich et al. |
| 3,991,754 A | 11/1976 | Gertzman |
| 4,005,251 A | 1/1977 | Tunc |
| 4,009,313 A | 2/1977 | Crawford et al. |
| 4,011,871 A | 3/1977 | Taft |
| 4,018,647 A | 4/1977 | Wietsma |
| 4,032,993 A | 7/1977 | Coquard et al. |
| 4,035,540 A | 7/1977 | Gander |
| 4,038,233 A | 7/1977 | Shultz |
| 4,073,777 A | 2/1978 | O'Neill et al. |
| 4,082,886 A | 4/1978 | Butterworth et al. |
| 4,084,033 A | 4/1978 | Drelich |
| 4,084,591 A | 4/1978 | Takebe et al. |
| 4,092,454 A | 5/1978 | Domoto et al. |
| 4,099,976 A | 7/1978 | Kraskin et al. |
| 4,112,167 A | 9/1978 | Dake et al. |
| 4,117,187 A | 9/1978 | Adams et al. |
| 4,136,798 A | 1/1979 | Oberstein |
| 4,141,713 A | 2/1979 | Ammannati et al. |
| 4,144,122 A | 3/1979 | Emanuelsson et al. |
| 4,154,883 A | 5/1979 | Elias |
| 4,157,724 A | 6/1979 | Persson |
| 4,186,233 A | 1/1980 | Krajewski et al. |
| 4,201,216 A | 5/1980 | Mattei |
| 4,226,753 A | 10/1980 | Lewis et al. |
| 4,245,744 A | 1/1981 | Daniels et al. |
| 4,258,849 A | 3/1981 | Miller |
| 4,264,289 A | 4/1981 | Day |
| 4,278,113 A | 7/1981 | Persson |
| 4,301,203 A | 11/1981 | Keuchel |
| 4,306,998 A | 12/1981 | Wenzel et al. |
| 4,332,319 A | 6/1982 | Hurwood |
| 4,336,345 A | 6/1982 | Lewis et al. |
| 4,343,134 A | 8/1982 | Davidowich et al. |
| 4,343,403 A | 8/1982 | Daniels |
| 4,344,804 A | 8/1982 | Bijen et al. |
| 4,352,649 A | 10/1982 | Jacobsen et al. |
| 4,353,687 A | 10/1982 | Nielsen |
| 4,356,229 A | 10/1982 | Brodnyan et al. |
| 4,372,447 A | 2/1983 | Miller |
| 4,377,544 A | 3/1983 | Rasmussen |
| 4,377,645 A | 3/1983 | Guthrie et al. |
| 4,385,019 A | 5/1983 | Bernstein et al. |
| 4,419,403 A | 12/1983 | Varona |
| 4,440,105 A | 4/1984 | Jeltema |
| 4,476,323 A | 10/1984 | Hellsten et al. |
| 4,491,645 A | 1/1985 | Thompson |
| 4,494,278 A | 1/1985 | Kroyer et al. |
| 4,496,618 A | 1/1985 | Okamoto |
| 4,501,641 A | 2/1985 | Hirakawa et al. |
| 4,511,687 A | 4/1985 | Nakanishi |
| 4,512,279 A | 4/1985 | Damrau et al. |
| 4,528,360 A | 7/1985 | Fujita et al. |
| 4,559,157 A | 12/1985 | Smith et al. |
| 4,575,891 A | 3/1986 | Valente |
| 4,585,835 A | 4/1986 | Saegusa |
| 4,588,400 A | 5/1986 | Ring et al. |
| 4,594,389 A | 6/1986 | Lal et al. |
| 4,600,404 A | 7/1986 | Sheldon et al. |
| 4,609,431 A | 9/1986 | Grose et al. |
| 4,617,235 A | 10/1986 | Shinonome et al. |
| 4,627,806 A | 12/1986 | Johnson |
| 4,627,950 A | 12/1986 | Matsui et al. |
| 4,638,017 A | 1/1987 | Larson et al. |
| 4,640,810 A | 2/1987 | Laursen et al. |
| 4,650,409 A | 3/1987 | Nistri et al. |
| 4,677,890 A | 7/1987 | Yannes |
| 4,690,821 A | 9/1987 | Smith et al. |
| 4,702,947 A | 10/1987 | Pall et al. |
| 4,724,980 A | 2/1988 | Farley |
| 4,725,489 A | 2/1988 | Jones et al. |
| 4,732,797 A | 3/1988 | Johnson et al. |
| 4,737,405 A | 4/1988 | Bouchette |
| 4,738,992 A | 4/1988 | Larson et al. |
| 4,740,398 A | 4/1988 | Bouchette |
| 4,753,844 A | 6/1988 | Jones et al. |
| 4,755,421 A | 7/1988 | Manning et al. |
| 4,772,492 A | 9/1988 | Bouchette |
| 4,772,501 A | 9/1988 | Johnson et al. |
| 4,781,974 A | 11/1988 | Bouchette et al. |
| 4,792,326 A | 12/1988 | Tews |
| 4,795,668 A | 1/1989 | Krueger et al. |
| 4,814,131 A | 3/1989 | Atlas |
| 4,837,078 A | 6/1989 | Harrington |
| 4,855,132 A | 8/1989 | Heller et al. |
| 4,894,118 A | 1/1990 | Edwards et al. |
| 4,930,942 A | 6/1990 | Keyes et al. |
| 4,966,808 A | 10/1990 | Kawano |
| 4,970,260 A | 11/1990 | Lundberg |
| 4,998,984 A | 3/1991 | McClendon |
| 5,009,652 A | 4/1991 | Morgan et al. |
| 5,033,172 A | 7/1991 | Harrington |
| 5,041,252 A | 8/1991 | Fujii et al. |
| 5,045,387 A | 9/1991 | Schmalz |
| 5,049,440 A | 9/1991 | Bornhoeft, III et al. |
| 5,053,482 A | 10/1991 | Tietz |
| 5,057,361 A | 10/1991 | Sayovitz et al. |
| 5,059,630 A | 10/1991 | Fujita et al. |
| 5,084,136 A | 1/1992 | Haines et al. |
| 5,096,640 A | 3/1992 | Brody et al. |
| 5,097,004 A | 3/1992 | Gallagher et al. |
| 5,097,005 A | 3/1992 | Tietz |
| 5,102,601 A | 4/1992 | Farris et al. |
| 5,104,367 A | 4/1992 | Hill |

| | | |
|---|---|---|
| 5,104,923 A | 4/1992 | Steinwand et al. |
| 5,120,598 A | 6/1992 | Robeson et al. |
| 5,145,727 A | 9/1992 | Potts et al. |
| 5,149,335 A | 9/1992 | Kellenberger et al. |
| 5,149,576 A | 9/1992 | Potts et al. |
| 5,171,308 A | 12/1992 | Gallagher et al. |
| 5,171,309 A | 12/1992 | Gallagher et al. |
| 5,171,402 A | 12/1992 | Haines et al. |
| 5,173,526 A | 12/1992 | Vijayendran et al. |
| 5,178,646 A | 1/1993 | Barber, Jr. et al. |
| 5,178,812 A | 1/1993 | Sanford et al. |
| 5,181,966 A | 1/1993 | Honeycutt et al. |
| 5,181,967 A | 1/1993 | Honeycutt |
| 5,182,162 A | 1/1993 | Andrusko |
| 5,196,470 A | 3/1993 | Anderson et al. |
| 5,200,037 A | 4/1993 | Noda |
| 5,205,968 A | 4/1993 | Damrow et al. |
| 5,206,064 A | 4/1993 | Scholz |
| 5,207,662 A | 5/1993 | James |
| 5,207,837 A | 5/1993 | Honeycutt |
| 5,208,098 A | 5/1993 | Stover |
| 5,216,050 A | 6/1993 | Sinclair |
| 5,217,495 A | 6/1993 | Kaplan et al. |
| 5,217,798 A | 6/1993 | Brady et al. |
| 5,219,646 A | 6/1993 | Gallagher et al. |
| 5,227,101 A | 7/1993 | Mahoney et al. |
| 5,245,785 A | 9/1993 | Taniguchi et al. |
| 5,246,647 A | 9/1993 | Beck et al. |
| 5,248,461 A | 9/1993 | Pluyter et al. |
| 5,256,417 A | 10/1993 | Koltisko |
| 5,257,982 A | 11/1993 | Cohen et al. |
| 5,264,269 A | 11/1993 | Kakiuchi et al. |
| 5,264,491 A | 11/1993 | Quirk |
| 5,270,358 A | 12/1993 | Asmus |
| 5,275,699 A | 1/1994 | Allan et al. |
| 5,281,306 A | 1/1994 | Kakiuchi et al. |
| 5,286,538 A | 2/1994 | Pearlstein et al. |
| 5,295,985 A | 3/1994 | Romesser et al. |
| 5,300,192 A | 4/1994 | Hansen et al. |
| 5,304,420 A | 4/1994 | Hirakawa et al. |
| 5,312,883 A | 5/1994 | Komatsu et al. |
| 5,317,063 A | 5/1994 | Komatsu et al. |
| 5,330,827 A | 7/1994 | Hansen |
| 5,330,832 A | 7/1994 | Liu |
| 5,334,176 A | 8/1994 | Buenger et al. |
| 5,342,335 A | 8/1994 | Rhim |
| 5,346,541 A | 9/1994 | Goldman et al. |
| 5,356,963 A | 10/1994 | Kauffman et al. |
| 5,360,826 A | 11/1994 | Egolf et al. |
| 5,366,804 A | 11/1994 | Dugan |
| 5,369,155 A | 11/1994 | Asmus |
| 5,384,189 A | 1/1995 | Kuroda et al. |
| 5,389,703 A | 2/1995 | Lee |
| 5,393,602 A | 2/1995 | Urry |
| 5,397,672 A * | 3/1995 | Larson et al. ............... 430/115 |
| 5,399,412 A | 3/1995 | Sudall et al. |
| 5,405,342 A | 4/1995 | Roessler et al. |
| 5,407,442 A | 4/1995 | Karapasha |
| 5,409,747 A | 4/1995 | Pearlstein et al. |
| 5,415,643 A | 5/1995 | Kolb |
| 5,415,813 A | 5/1995 | Misselyn et al. |
| 5,427,899 A | 6/1995 | Avison et al. |
| 5,429,686 A | 7/1995 | Chiu et al. |
| 5,437,908 A | 8/1995 | Demura et al. |
| 5,441,841 A * | 8/1995 | Larson et al. ............ 162/181.7 |
| 5,442,016 A | 8/1995 | Jarrett |
| 5,445,785 A | 8/1995 | Rhim |
| 5,458,591 A | 10/1995 | Roessler et al. |
| 5,459,007 A * | 10/1995 | Larson et al. ............ 162/181.7 |
| 5,466,410 A | 11/1995 | Hills |
| 5,466,518 A | 11/1995 | Isaac et al. |
| 5,470,640 A | 11/1995 | Modrak |
| 5,470,941 A | 11/1995 | Kim et al. |
| 5,473,789 A | 12/1995 | Oster |
| 5,476,457 A | 12/1995 | Roessler et al. |
| 5,476,909 A | 12/1995 | Kim |
| 5,486,307 A | 1/1996 | Misselyn et al. |
| 5,486,418 A | 1/1996 | Ohmory et al. |
| 5,492,599 A | 2/1996 | Olson et al. |
| 5,500,068 A | 3/1996 | Srinivasan et al. |
| 5,500,281 A | 3/1996 | Srinivasan et al. |
| 5,509,913 A | 4/1996 | Yeo et al. |
| 5,514,380 A | 5/1996 | Song |
| 5,519,085 A | 5/1996 | Ma |
| 5,522,841 A | 6/1996 | Roby |
| 5,525,449 A * | 6/1996 | Spiewak et al. ............. 430/115 |
| 5,530,074 A | 6/1996 | Jarrett |
| 5,532,300 A | 7/1996 | Koubek et al. |
| 5,532,306 A | 7/1996 | Kauffman et al. |
| 5,534,178 A | 7/1996 | Bailly et al. |
| 5,542,566 A | 8/1996 | Glaug et al. |
| 5,545,472 A | 8/1996 | Koubek et al. |
| 5,569,230 A | 10/1996 | Fisher et al. |
| 5,573,637 A | 11/1996 | Ampulski et al. |
| 5,576,364 A | 11/1996 | Isaac et al. |
| 5,578,344 A | 11/1996 | Ahr et al. |
| 5,582,704 A | 12/1996 | Valko et al. |
| 5,589,545 A | 12/1996 | Ramachandran |
| 5,604,195 A | 2/1997 | Misselyn et al. |
| 5,607,550 A | 3/1997 | Akers |
| 5,607,551 A | 3/1997 | Farrington, Jr. et al. |
| 5,612,404 A | 3/1997 | Das et al. |
| 5,613,959 A | 3/1997 | Roessler et al. |
| 5,616,201 A | 4/1997 | Finch et al. |
| 5,618,911 A | 4/1997 | Kimura et al. |
| 5,620,788 A | 4/1997 | Garavaglia et al. |
| 5,629,081 A | 5/1997 | Richards et al. |
| 5,631,317 A | 5/1997 | Komatsu et al. |
| 5,633,297 A | 5/1997 | Valko et al. |
| 5,647,862 A | 7/1997 | Osborn, III et al. |
| 5,647,863 A | 7/1997 | Hammons et al. |
| 5,649,336 A | 7/1997 | Finch et al. |
| 5,660,928 A | 8/1997 | Stokes et al. |
| 5,670,110 A | 9/1997 | Dirk et al. |
| 5,672,248 A | 9/1997 | Wendt et al. |
| 5,684,075 A | 11/1997 | Patel et al. |
| 5,693,698 A | 12/1997 | Patel et al. |
| 5,695,551 A | 12/1997 | Buckingham et al. |
| 5,698,322 A | 12/1997 | Tsai et al. |
| 5,714,157 A | 2/1998 | Sandell et al. |
| 5,725,789 A | 3/1998 | Huber et al. |
| 5,725,821 A | 3/1998 | Gannon et al. |
| 5,753,246 A | 5/1998 | Peters |
| 5,756,112 A | 5/1998 | Mackey |
| 5,763,044 A | 6/1998 | Ahr et al. |
| 5,763,332 A | 6/1998 | Gordon et al. |
| 5,765,717 A | 6/1998 | Gottselig |
| 5,766,758 A | 6/1998 | Hirakawa et al. |
| 5,770,528 A | 6/1998 | Mumick et al. |
| 5,786,065 A | 7/1998 | Annis et al. |
| 5,795,921 A | 8/1998 | Dyer et al. |
| 5,800,417 A | 9/1998 | Goerg-Wood et al. |
| 5,837,627 A | 11/1998 | Halabisky et al. |
| 5,846,230 A | 12/1998 | Osborn, III et al. |
| 5,849,805 A | 12/1998 | Dyer |
| 5,866,675 A | 2/1999 | Ahmed et al. |
| 5,869,596 A | 2/1999 | Ahmed et al. |
| 5,871,763 A | 2/1999 | Luu et al. |
| 5,891,126 A | 4/1999 | Osborn, III et al. |
| 5,899,893 A | 5/1999 | Dyer et al. |
| 5,905,046 A | 5/1999 | Takeda et al. |
| 5,916,678 A | 6/1999 | Jackson et al. |

| | | | |
|---|---|---|---|
| 5,935,384 A | 8/1999 | Taniguchi | |
| 5,935,880 A | 8/1999 | Wang et al. | |
| 5,948,710 A | 9/1999 | Pomplun et al. | |
| 5,952,077 A | 9/1999 | Booth et al. | |
| 5,952,251 A | 9/1999 | Jackson et al. | |
| 5,958,187 A | 9/1999 | Bhat et al. | |
| 5,958,555 A | 9/1999 | Takeuchi et al. | |
| 5,959,016 A | 9/1999 | Schmidt et al. | |
| 5,969,052 A | 10/1999 | Mumick et al. | |
| 5,971,138 A | 10/1999 | Soughan | |
| 5,972,805 A | 10/1999 | Pomplun et al. | |
| 5,980,673 A | 11/1999 | Takeuchi et al. | |
| 5,981,070 A | 11/1999 | Ishizaki et al. | |
| 5,986,004 A | 11/1999 | Pomplun et al. | |
| 5,997,952 A | 12/1999 | Harris et al. | |
| 6,005,045 A | 12/1999 | Klanica | |
| 6,010,972 A | 1/2000 | Zacharias et al. | |
| 6,017,832 A | 1/2000 | Yahiaoui et al. | |
| 6,025,404 A | 2/2000 | Harris et al. | |
| 6,028,016 A | 2/2000 | Yahiaoui et al. | |
| 6,031,045 A | 2/2000 | Wei et al. | |
| 6,037,407 A | 3/2000 | Derian et al. | |
| 6,040,049 A | 3/2000 | Tominaga et al. | |
| 6,042,769 A | 3/2000 | Gannon et al. | |
| 6,043,317 A | 3/2000 | Mumick et al. | |
| 6,051,749 A | 4/2000 | Schulz | |
| 6,056,235 A | 5/2000 | Brozinsky | |
| 6,059,882 A | 5/2000 | Steinhardt et al. | |
| 6,059,928 A | 5/2000 | Van Luu et al. | |
| 6,071,451 A | 6/2000 | Wang et al. | |
| 6,083,854 A | 7/2000 | Bogdanski et al. | |
| 6,090,472 A | 7/2000 | Wang et al. | |
| 6,098,836 A | 8/2000 | Gottselig | |
| 6,103,858 A | 8/2000 | Yamamoto et al. | |
| 6,121,170 A | 9/2000 | Tsai et al. | |
| 6,123,811 A | 9/2000 | Komarnycky et al. | |
| 6,127,593 A | 10/2000 | Bjorkquist et al. | |
| 6,132,557 A | 10/2000 | Takeuchi et al. | |
| 6,179,962 B1 | 1/2001 | Brady et al. | |
| 6,187,141 B1 | 2/2001 | Takeuchi et al. | |
| 6,190,502 B1 | 2/2001 | Takeuchi et al. | |
| 6,194,517 B1 | 2/2001 | Pomplun et al. | |

FOREIGN PATENT DOCUMENTS

| | | |
|---|---|---|
| EP | 0 419 654 A1 | 4/1991 |
| EP | 0 525671 A1 | 2/1993 |
| EP | 0 358 313 B1 | 8/1993 |
| EP | 0 241 127 B1 | 10/1993 |
| EP | 0 372 388 B1 | 2/1994 |
| EP | 0 582 123 B1 | 2/1994 |
| EP | 0 601 518 A1 | 6/1994 |
| EP | 0 608 460 B1 | 8/1994 |
| EP | 0 613 675 A1 | 9/1994 |
| EP | 0 634 466 A2 | 9/1994 |
| EP | 0 619 074 A1 | 10/1994 |
| EP | 0 619 341 B1 | 10/1994 |
| EP | 0 620 256 A2 | 10/1994 |
| EP | 0 421 163 B1 | 11/1994 |
| EP | 0 572 569 B1 | 12/1994 |
| EP | 0634284 A * | 1/1995 |
| EP | 0 634 284 | 1/1995 |
| EP | 0 638 679 B1 | 2/1995 |
| EP | 0 639 381 A1 | 2/1995 |
| EP | 0 507 878 B1 | 4/1995 |
| EP | 0 648 871 A1 | 4/1995 |
| EP | 0 445 655 B1 | 6/1995 |
| EP | 0 411 752 B1 | 7/1995 |
| EP | 0 552 762 B1 | 8/1995 |
| EP | 0 672 787 A2 | 9/1995 |
| EP | 0 689 817 A2 | 1/1996 |
| EP | 0 597 978 B1 | 3/1996 |
| EP | 0 726 068 A2 | 8/1996 |
| EP | 0 580 764 B1 | 1/1997 |
| EP | 0 761 795 A2 | 3/1997 |
| EP | 0 765 649 A2 | 4/1997 |
| EP | 0 768 425 A2 | 4/1997 |
| EP | 0 225 800 B1 | 5/1997 |
| EP | 0 443 627 B1 | 6/1997 |
| EP | 0 510 572 B1 | 6/1997 |
| EP | 0 779 387 A2 | 6/1997 |
| EP | 0 781 538 A2 | 7/1997 |
| EP | 0 801 157 A2 | 10/1997 |
| EP | 0 802 282 A4 | 10/1997 |
| EP | 0 807 704 A1 | 11/1997 |
| EP | 0 598 204 B1 | 12/1997 |
| EP | 0 531 112 B1 | 3/1998 |
| EP | 0 835 957 A2 | 4/1998 |
| EP | 0 549 988 B1 | 6/1998 |
| EP | 0 637 950 B1 | 7/1998 |
| EP | 0 766 756 B1 | 9/1998 |
| EP | 0 864 418 A2 | 9/1998 |
| EP | 0 873 100 B1 | 10/1998 |
| EP | 0 875 233 A1 | 11/1998 |
| EP | 0 792 144 B1 | 12/1998 |
| EP | 0 706 361 B1 | 3/1999 |
| EP | 0 904 933 A2 | 3/1999 |
| EP | 0 905 313 A2 | 3/1999 |
| EP | 0 671 496 B1 | 4/1999 |
| EP | 0 580 811 B1 | 8/1999 |
| EP | 0 693 915 B1 | 9/1999 |
| EP | 0 699 727 B1 | 9/1999 |
| EP | 0 945 536 A2 | 9/1999 |
| EP | 0 766 755 B1 | 12/1999 |
| EP | 0 793 743 B1 | 3/2000 |
| EP | 1 024 225 A1 | 8/2000 |
| EP | 1 050 297 A2 | 8/2000 |
| EP | 1 046 747 A1 | 10/2000 |
| EP | 1 065 302 A1 | 1/2001 |
| FR | 2672788 | 8/1992 |
| JP | 4943114 | 11/1974 |
| JP | 51-3248 A | 1/1976 |
| JP | 52 128937 | 10/1977 |
| JP | 81-35703 A | 8/1981 |
| JP | 63 270893 | 11/1988 |
| JP | 04 046915 | 2/1992 |
| JP | 04 309510 | 11/1992 |
| JP | 5125123 A1 | 5/1993 |
| JP | 6172453 A1 | 6/1994 |
| JP | 61-92527 B1 | 7/1994 |
| JP | 62-07162 B1 | 7/1994 |
| JP | 06220793 A | 8/1994 |
| JP | 62-33809 B1 | 8/1994 |
| JP | 08113823 A | 5/1996 |
| JP | 8239428 A1 | 9/1996 |
| JP | 10 204792 | 8/1998 |
| JP | 11 279983 | 10/1999 |
| RU | 705013 | 12/1979 |
| WO | WO 90/03156 A1 | 4/1990 |
| WO | WO 93/07199 A1 | 4/1993 |
| WO | WO 94/25189 A1 | 11/1994 |
| WO | WO 95/18191 A1 | 7/1995 |
| WO | WO 96/06119 | 2/1996 |
| WO | WO 96/12615 A1 | 5/1996 |
| WO | WO 96/30576 A1 | 10/1996 |
| WO | WO 97/02375 A1 | 1/1997 |
| WO | WO 97/02376 A1 | 1/1997 |
| WO | WO 97/10100 A1 | 3/1997 |
| WO | WO 97/16597 A1 | 5/1997 |
| WO | WO 97/18784 A1 | 5/1997 |
| WO | WO 97/47227 A1 | 12/1997 |
| WO | WO 98/26808 A1 | 6/1998 |
| WO | WO 98/29501 A1 | 7/1998 |

| | | | | | | |
|---|---|---|---|---|---|---|
| WO | WO 98/29501 | 7/1998 | | WO | WO 99/07273 A1 | 2/1999 |
| WO | WO 98/36117 A1 | 8/1998 | | WO | WO 99/25318 A1 | 5/1999 |
| WO | WO 98/41577 | 9/1998 | | WO | WO 00/00026 A1 | 1/2000 |
| WO | WO 98/41577 A1 | 9/1998 | | WO | WO 00/38751 A1 | 7/2000 |
| WO | WO 98/44181 A1 | 10/1998 | | WO | WO 00/39378 A2 | 7/2000 |
| WO | WO 98/48684 A1 | 11/1998 | | WO | WO 00/39378 | 7/2000 |
| WO | WO 98/52698 A | * 11/1998 | | WO | WO 01/13880 A1 | 3/2001 |
| WO | WO 98/52698 | 11/1998 | | WO | WO 01/35923 A1 | 5/2001 |
| WO | WO 98/53006 A1 | 11/1998 | | WO | WO 01/83666 A2 | 11/2001 |
| WO | WO 99/01106 A1 | 1/1999 | | | | |
| WO | WO 99/06523 A1 | 2/1999 | | * cited by examiner | | |

WATER-DISPERSIBLE, CATIONIC POLYMERS, A METHOD OF MAKING SAME AND ITEMS USING SAME

FIELD OF THE INVENTION

The present invention is directed to ion-sensitive or triggerable, water-dispersible or water-soluble cationic polymers and polymer formulations. The present invention is also directed to a method of making ion-sensitive or triggerable, water-dispersible or water-soluble cationic polymers and polymer formulations and their applicability as binder compositions for disposable items. The present invention is further directed to disposable items, such as wet-wipes comprising ion-sensitive or triggerable, water-dispersible binder compositions including cationic polymer or polymer formulations.

BACKGROUND OF THE INVENTION

For many years, the problem of disposability has plagued industries which provide disposable items, such as, diapers, wet wipes, incontinent garments and feminine care products. While much headway has been made in addressing this problem, one of the weak links has been the inability to create an economical coherent fibrous web, which will readily dissolve or disintegrate in water, but still have sufficient in-use strength. See, for example, U.K. patent disclosure 2,241,373 and U.S. Pat. No. 4,186,233. Without such a product, the ability of the user to dispose of the product by flushing it down the toilet is greatly reduced, if not eliminated. Furthermore, the ability of the product to disintegrate in a landfill is quite limited because a large portion of the product components, which may well be biodegradable or photodegradable, are encapsulated in or bound together by plastic which degrades over a long period of time, if at all. Accordingly, if the plastic disintegrated in the presence of water, the internal components could degrade as a result of the rupture of the plastic encapsulation or binding.

Disposable products, such as diapers, feminine care products and adult incontinent care products may be made to be disposed by flushing down toilets. Usually such products comprise a body side liner which must rapidly pass fluids, such as urine or menses, so that the fluid may be absorbed by an absorbent core of the product. Typically, the body side liner may be a coherent fibrous web, which desirably possesses a number of characteristics, such as softness and flexibility. The fibrous web of the body side liner material may be typically formed by wet or dry (air) laying a generally random plurality of fibers and joining them together to form a coherent web with a binder compositions. Past binder compositions have preformed this function well. However, fibrous webs comprising these compositions tended to be non-dispersible and present problems in typical household sanitation systems.

Recent binder compositions have been developed which can be more dispersible and are more environmentally responsible than past binder compositions. One class of binder compositions includes polymeric materials having inverse solubility in water. These binder compositions are insoluble in warm water, but are soluble in cold water, such as found in a toilet. It is well known that a number of polymers exhibit cloud points or inverse solubility properties in aqueous media. These polymers have been cited in several publications for various applications, including (1) as evaporation retarders (JP 6207162); (2) as temperature sensitive compositions, which are useful as temperature indicators due to a sharp color change associated with a corresponding temperature change (JP 6192527); (3) as heat sensitive materials that are opaque at a specific temperature and become transparent when cooled to below the specific temperature (JP 51003248 and JP 81035703); (4) as wound dressings with good absorbing characteristics and easy removal (JP 6233809); and (5) as materials in flushable personal care products (U.S. Pat. No. 5,509,913, issued to Richard S. Yeo on Apr. 23, 1996 and assigned to Kimberly-Clark Corporation).

Other recent binders of interest include a class of binders, which are ion-sensitive. Several U.S. and European patents assigned to Lion Corporation of Tokyo, Japan, disclose ion-sensitive polymers comprising acrylic acid and alkyl or aryl acrylates. See U.S. Pat. Nos. 5,312,883, 5,317,063 and 5,384,189, the disclosures of which are incorporated herein by reference, as well as, European Pat. No. 608460A1. In U.S. Pat. No. 5,312,883, terpolymers are disclosed as suitable binders for flushable nonwoven webs. The disclosed acrylic acid-based terpolymers, which comprise partially neutralized acrylic acid, butyl acrylate and 2-ethylhexyl acrylate, are suitable binders for use in flushable nonwoven webs in some parts of the world. However, because of the presence of a small amount of sodium acrylate in the partially neutralized terpolymer, these binders fail to disperse in water containing more than about 15 ppm $Ca^{2+}$ and $Mg^{2+}$. When placed in water containing more than about 15 ppm $Ca^{2+}$ and/or $Mg^{2+}$ ions, nonwoven webs using the above-described binders maintain a tensile strength greater than 30 g/in, which negatively affects the "dispersibility" of the web. The proposed mechanism for the failure is that each calcium ion binds with two carboxylate groups either intramolecularly or intermolecularly. Intramolecular association causes the polymer chain to coil up, which eventually leads to polymer precipitation. Intermolecular association yields crosslinking. Whether intramolecular or intermolecular associations are taking place, the terpolymer is not soluble in water containing more than about 15 ppm $Ca^{2+}$ and/or $Mg^{2+}$. Due to the strong interaction between calcium ions and the carboxylate groups of the terpolymer, dissociation of the complex is highly unlikely because this association is irreversible. Therefore, the above-described polymer that has been exposed to a high $Ca^{2+}$ and/or $Mg^{2+}$ concentration solution will not disperse in water even if the calcium concentration decreases. This limits the application of the polymer as a flushable binder material because most areas across the U.S. have hard water, which contains more than 15 ppm $Ca^{2+}$ and/or $Mg^{2+}$.

In a co-pending application assigned to Kimberly Clark; i.e., U.S. patent application Ser. No. 09/223,999, filed Dec. 31, 1998, the disclosure of which is incorporated herein by reference, there is disclosed a modification of the acrylic acid terpolymers of the above-referenced patents to Lion Corporation. Specifically, U.S. patent application Ser. No. 09/223,999 discloses a sulfonate anion modified acrylic acid terpolymers which has improved dispersibility in relatively hard water; e.g., up to 200 ppm $Ca^{2+}$ and/or $Mg^{2+}$, compared to the unmodified Lion polymers. The wetted sheet is flexible and soft. However, the Lion Corporation ion-sensitive polymers of the above-referenced patents and the sulfonate anion modified acrylic acid terpolymers of the co-pending application, when used as binders for personal care products, such as wet wipes, typically have reduced initial sheet wettability, increased dry sheet stiffness, increased sheet stickiness, reduced binder sprayability and relatively high product cost.

Another approach to dispersible personal care products is disclosed in U.S. Pat. No. 5,281,306 to Kao Corporation of Tokyo, Japan. This patent discloses a water-disintegratable cleansing sheet; i.e., wet wipe, comprising water-dispersible fibers treated with a water-soluble binder having a carboxyl group. The cleansing sheet is treated with a cleansing agent containing 5%–95% of a water-compatible organic solvent, a salt and 95%–5% water. A preferred organic solvent is propylene glycol. The cleansing sheet retains wet strength and does not disperse in the organic solvent-based cleansing agent, but disperses in water. However, because of the high viscosity of carboxymethylcellulose, which makes it difficult to apply to fibrous webs, the presence of an organic solvent, and the sensitivity to hard water, the composition of this patent has little commercial applicability.

Although many patents disclose various ion and temperature sensitive compositions for water-dispersible or flushable materials, there exists a need for dispersible products possessing softness, flexibility, three dimensionality, and resiliency; wicking and structural integrity in the presence of body fluids (including feces) at body temperature; and true fiber dispersion after toilet flushing so that product does not become entangled with tree roots or at bends in sewer pipes. Moreover, there is a need in the art for flushable products having water-dispersibility in all areas of the world, including soft and hard water areas. Furthermore, there is a need for water-dispersible binders that do not reduce wettability of product with which they are used and are sprayable for relatively easy and uniform application to and penetration into products. Finally, there is a need for water-dispersible, flushable wet wipes that are stable during storage and retain a desired level of wet strength during use and are wetted with a wetting composition that is relatively free, or is substantially free, of organic solvents. Such a product is needed at a reasonable cost without compromising product safety and environmental concerns, something that past products have failed to do.

SUMMARY OF THE INVENTION

The present invention is directed to ion-sensitive cationic polymers and polymer formulations and to triggerable cationic polymers and polymer formulations, which have been developed to address the above-described problems associated with currently available, ion-sensitive polymers and other polymers described in literature. The ion-sensitive polymer formulations of the present invention have a "trigger property," such that the polymers are insoluble in a wetting composition comprising an insolublizing agent of a particular type and concentration, such as monovalent salt solutions at concentrations above about 2%, but are soluble when diluted with water including hard water with up to 200 ppm (parts per million) calcium and magnesium ions. Unlike some ion-sensitive polymer formulations, which lose dispersibility in hard water because of ion cross-linking by calcium ions, the ion-sensitive cationic polymer formulations of the present invention are insensitive to calcium and/or magnesium ions at concentrations of a few hundred ppm and are insensitive to pH variations. The ion specific cationic polymers and polymer formulations of the present invention have a "trigger property," such that the polymers are insoluble in a wetting composition comprising an insolublizing agent of a particular type and concentration, such as a divalent metal salt capable of forming complex anion in solution at concentrations above about 0.5%, but are soluble when diluted with water including other ions, such as divalent salt solutions as found in hard water with up to 200 ppm (parts per million) calcium and magnesium ions. Consequently, flushable products containing the polymer formulations of the present invention maintain dispersibility in hard water or soft water.

The polymer formulations of the present invention are useful as binders and structural components for air-laid and wet-laid nonwoven fabrics for applications, such as body-side liners, fluid distribution materials, fluid intake materials (surge) or cover stock in various personal care products. The polymer formulations of the present invention are particularly useful as a binder material for flushable personal care products, particularly wet wipes for personal use, such as cleaning or treating skin, make-up removal, nail polish removal, medical care, and also wipes for use in hard surface cleaning, automotive care, including wipes comprising cleaning agents, disinfectants, and the like. The flushable products maintain integrity or wet strength during storage and use, and break apart or disperse after disposal in the toilet when the salt or ion concentration falls below a critical level. Suitable substrates for treatment include tissue, such as creped or uncreped tissue, coform products, hydroentangled webs, airlaid mats, fluff pulp, nonwoven webs, and composites thereof. Methods for producing uncreped tissues and molded three-dimensional tissue webs of use in the present invention can be found in commonly owned U.S. patent application, Ser. No. 08/912,906, "Wet Resilient Webs and Disposable Articles Made Therewith," by F.-J. Chen et al., filed Aug. 15, 1997; U.S. Pat. No. 5,429,686, issued to Chiu et al. on Jul. 4, 1995; U.S. Pat. No. 5,399,412, issued to S. J. Sudall and S. A. Engel on Mar. 21, 1995; U.S. Pat. No. 5,672,248, issued to Wendt et al. on Sep. 30, 1997; and U.S. Pat. No. 5,607,551, issued to Farrington et al. on Mar. 4, 1997; all of which are incorporated herein by reference in their entirety. The molded tissue structures of the above patents can be especially helpful in providing good cleaning in a wet wipe. Good cleaning can also be promoted by providing a degree of texture in other substrates as well by embossing, molding, wetting and through-air drying on a textured fabric, and the like. The cationic polymers and polymer formulations of the present invention are particularly useful as a binder for fibrous materials because the polymers and polymer formulations are substantive to the fibers.

Airlaid material can be formed by metering an airflow containing the fibers and other optional materials, in substantially dry condition, onto a typically horizontally moving wire forming screen. Suitable systems and apparatus for air-laying mixtures of fibers and thermoplastic material are disclosed in, for example, U.S. Pat. No. 4,157,724 (Persson), issued Jun. 12, 1979, and reissued Dec. 25, 1984 as Re. U.S. Pat. No. 31,775; U.S. Pat. No. 4,278,113 (Persson), issued Jul. 14, 1981; U.S. Pat. No. 4,264,289 (Day), issued Apr. 28, 1981; U.S. Pat. No. 4,352,649 (Jacobsen et al.), issued Oct. 5, 1982; U.S. Pat. No. 4,353,687 (Hosler, et al.), issued Oct. 12, 1982; U.S. Pat. No. 4,494,278 (Kroyer, et al.), issued Jan. 22, 1985; U.S. Pat. No. 4,627,806 (Johnson), issued Dec. 9, 1986; U.S. Pat. No. 4,650,409 (Nistri, et al.), issued Mar. 17, 1987; and U.S. Pat. No. 4,724,980 (Farley), issued Feb. 16, 1988; and U.S. Pat. No. 4,640,810 (Laursen et al.), issued Feb. 3, 1987, the disclosures of which are all incorporated herein by reference.

The present invention also discloses how to make water-dispersible nonwovens, including cover stock (liner), intake (surge) materials and wet wipes, which are stable in fluids having a first ionic composition, such as monovalent ions or divalent metal complex anions at a particular concentration substantially greater than is found in typical hard water or soft water, using the above-described unique polymer formulations as binder compositions. The resultant nonwovens are flushable and water-dispersible due to the tailored ion sensitivity, which can be triggered regardless of the hardness of water found in toilets throughout the United States and the world.

The present invention further discloses an improved wetting composition for wet wipes. Wet wipes employing the polymer formulations of the present invention are stable during storage and retain a desired level of wet strength during use and are wetted with a wetting composition or cleaning agent that can be relatively free, or is substantially free, of organic solvents.

These and other objects, features and advantages of the present invention will become apparent after a review of the following detailed description of the disclosed embodiments and the appended claims.

DETAILED DESCRIPTION OF THE DISCLOSED EMBODIMENTS

The present invention can be practiced using two different triggerable cationic polymers or polymer compositions. One triggerable, cationic polymer composition is an ion-sensitive cationic polymer composition and the other is an ion-specific cationic polymer and polymer composition. These two systems will be discussed further below. Each of these cationic polymer compositions may also optionally include a co-binder, which may be used to alter one or more of the physical properties of the cationic polymer composition.

In order to be an effective ion-sensitive or triggerable cationic polymer or cationic polymer formulation suitable for use in flushable or water-dispersible personal care products, the formulations should desirably be (1) functional; i.e., maintain wet strength under controlled conditions and dissolve or disperse rapidly in soft or hard water, such as found in toilets and sinks around the world; (2) safe (not toxic); and (3) relatively economical. In addition to the foregoing factors, the ion-sensitive or triggerable formulations when used as a binder composition for a non-woven substrate, such as a wet wipe, desirably should be (4) processable on a commercial basis; i.e., may be applied relatively quickly on a large scale basis, such as by spraying (which thereby requires that the binder composition have a relatively low viscosity at high shear); and (5) provide acceptable levels of sheet or substrate wettability. The wetting composition with which the wet wipes of the present invention are treated can provide some of the foregoing advantages, and, in addition, can provide one or more of (6) improved skin care, such as reduced skin irritation or other benefits, (7) improved tactile properties, and (8) promote good cleaning by providing a balance in use between friction and lubricity on the skin (skin glide). The ion-sensitive or triggerable cationic polymers and polymer formulations of the present invention and articles made therewith, especially wet wipes comprising particular wetting compositions set forth below, can meet many or all of the above criteria. Of course, it is not necessary for all of the advantages of the preferred embodiments of the present invention to be met to fall within the scope of the present invention.

Ion-Sensitive Cationic Polymer Compositions

The ion-sensitive cationic polymers of the present invention may be formed from two, three or four different monomers. The copolymers of the present invention are the polymerization product of a cationic monomer and at least one hydrophobic monomer. The terpolymers or tetrapolymers of the present invention are the polymerization products of a cationic monomer, at least one hydrophobic monomer and optionally at least one hydrophilic monomer or water-soluble nonionic monomer.

The preferred cationic polymer in the ion-sensitive cationic polymers of the present invention is [2-(methacryloyloxy)ethyl] trimethyl ammonium chloride.

Suitable hydrophobic monomers for use in the ion-sensitive cationic polymers of the present invention include, but are not limited to, alkyl acrylates, such as, butyl acrylate, 2-ethylhexyl acrylate, ethyl acrylate, lauryl acrylate, and hexadecyl acrylate. Methacrylate analogs of alkyl acrylates are also suitable.

Suitable hydrophilic monomers or water-soluble nonionic monomers for use in the ion-sensitive cationic polymers of the present invention include, but are not limited to, acrylamide and methacrylamide based monomers, such as acrylamide, N,N-dimethyl acrylamide, N-ethyl acrylamide, N-isopropyl acrylamide, and hydroxymethyl acrylamide; and acrylate or methacrylate based monomers include, such as, hydroxyalkyl acrylates and hydroxyalkyl methacrylates, such as hydroxyethyl methacrylate, hydroxyethyl acrylate; polyalkoxyl acrylates, such as polyethyleneglycol acrylates and polyalkoxyl methacrylates, such as polyethyleneglycol methacrylates ("PEG-MA"). Other suitable hydrophilic monomers or water-soluble nonionic monomers for use in the ion-sensitive cationic polymers of the present invention include, but are not limited to, N-vinylpyrrolidinone; and N-vinylformamide.

A preferred quaternary polymer of the present invention is the polymerization product of the following four monomers: acrylamide, butyl acrylate, 2-ethylhexyl acrylate and [2-(methacryloyloxy)ethyl] trimethyl ammonium chloride. A preferred terpolymer of the present invention is formed from three different monomers: butyl acrylate, 2-ethylhexyl acrylate and [2-(methacryloyloxy)ethyl] trimethyl ammonium chloride. A preferred copolymer of the present invention is the polymerization product of [2-(methacryloyloxy)ethyl] trimethyl ammonium chloride and butyl acrylate or 2-ethylhexyl acrylate. An especially preferred terpolymer of the present invention is the polymerization product of [2-(methacryloyloxy)ethyl] trimethyl ammonium chloride and butyl acrylate and 2-ethylhexyl acrylate. Acrylamide, [2-(methacryloyloxy)ethyl] trimethyl ammonium chloride, butyl acrylate and 2-ethylhexyl acrylate are all commercially available from Aldrich Chemical, Milwaukee, Wis.

For the ion-sensitive quaternary polymer made from acrylamide, butyl acrylate, 2-ethylhexyl acrylate and [2-(methacryloyloxy)ethyl] trimethyl ammonium chloride, the mole percent of monomer in the quaternary polymer is as follows: about 35 to less than 80 mole percent acrylamide; greater than 0 to about 45 mole percent butyl acrylate; greater than 0 to about 65 mole percent 2-ethylhexyl acrylate; and greater than 0 to about 20 mole percent [2-(methacryloyloxy)ethyl] trimethyl ammonium chloride. More specifically, the mole percent of monomers in the quaternary polymer is from about 50 to about 67 mole percent acrylamide; from about 15 to about 28 mole percent butyl acrylate; from about 7 to about mole 15 percent 2-ethylhexyl acrylate; and from greater than 0 to about 10 mole percent [2-(methacryloyloxy)ethyl] trimethyl ammonium chloride. Most specifically, the mole percent of monomers in the quaternary polymer is from about 57 to about 66 mole percent acrylamide; from about 15 to about 28 mole percent butyl acrylate; from about 7 to about 13 mole percent 2-ethylhexyl acrylate; and about 1 to about 6 mole percent [2-(methacryloyloxy)ethyl] trimethyl ammonium chloride.

For the ion-sensitive co- and terpolymer made from butyl acrylate, 2-ethylhexyl acrylate and [2-(methacryloyloxy)

ethyl] trimethyl ammonium chloride, the mole percent of monomer in the terpolymer is as follows: from 0 to about 90 mole percent butyl acrylate; from 0 to about 75 mole percent 2-ethylhexyl acrylate; and from 5 to about 60 mole percent [2-(methacryloyloxy)ethyl] trimethyl ammonium chloride.

The ion-sensitive terpolymers and quaternary polymers of the present invention may have an average molecular weight, which varies depending on the ultimate use of the polymer. The quaternary polymers of the present invention have a weight average molecular weight ranging from about 10,000 to about 5,000,000. More specifically, the quaternary polymers of the present invention have a weight average molecular weight ranging from about 25,000 to about 2,000,000, or, more specifically still, from about 200,000 to about 1,000,000. The terpolymers of the present invention have a weight average molecular weight ranging from about 10,000 to about 5,000,000. More specifically, the terpolymers of the present invention have a weight average molecular weight ranging from about 25,000 to about 2,000,000, or, more specifically still, from about 200,000 to about 1,000,000.

The ion-sensitive terpolymers and quaternary polymers of the present invention may be prepared according to a variety of polymerization methods, desirably a solution polymerization method. Suitable solvents for the polymerization method include, but are not limited to, lower alcohols such as methanol, ethanol and propanol; a mixed solvent of water and one or more lower alcohols mentioned above; and a mixed solvent of water and one or more lower ketones such as acetone or methyl ethyl ketone.

In the polymerization methods of the present invention, any free radical polymerization initiator may be used. Selection of a particular initiator may depend on a number of factors including, but not limited to, the polymerization temperature, the solvent, and the monomers used. Suitable polymerization initiators for use in the present invention include, but are not limited to, 2,2'-azobisisobutyronitrile, 2,2'-azobis(2-methylbutyronitrile), 2,2'-azobis(2,4-dimethylvaleronitrile), 2,2'-azobis(2-amidinopropane) dihydrochloride, 2,2'-azobis(N,N'-dimethyleneisobutylamidine), potassium persulfate, ammonium persulfate, and aqueous hydrogen peroxide. The amount of polymerization initiator may desirably range from about 0.01 to 5 weight percent based on the total weight of monomer present.

The polymerization temperature may vary depending on the polymerization solvent, monomers, and initiator used, but in general, ranges from about 20° C. to about 90° C. Polymerization time generally ranges from about 2 to about 8 hours.

In a further embodiment of the present invention, the above-described ion-sensitive cationic polymer formulations are used as binder materials for flushable and/or non-flushable products. In order to be effective as a binder material in flushable products throughout the United States, the ion-sensitive polymer formulations of the present invention remain stable and maintain their integrity while dry or in relatively high concentrations of monovalent ions, but become soluble in water containing up to about 200 ppm or more divalent ions, especially calcium and magnesium. Desirably, the ion-sensitive cationic polymer formulations of the present invention are insoluble in a salt solution containing at least about 2 weight percent of one or more inorganic and/or organic salts containing monovalent and/or multivalent ions. More desirably, the ion-sensitive cationic polymer formulations of the present invention are insoluble in a salt solution containing from about 2 weight percent to about 5 weight percent of one or more inorganic and/or organic salts containing monovalent and/or multivalent ions. Even more desirably, the ion-sensitive polymer formulations of the present invention are insoluble in salt solutions containing from about 2 weight percent to about 4 weight percent of one or more inorganic and/or organic salts containing monovalent and/or multivalent ions. Suitable monovalent ions include, but are not limited to, $Na^+$ ions, $K^+$ ions, $Li^+$ ions, $NH_4^+$ ions, low molecular weight quaternary ammonium compounds (e.g., those having fewer than 5 carbons on any side group), and a combination thereof. Suitable multivalent ions include, but are not limited to, $Zn^{2+}$ and $Ca^{2+}$.

Based on a recent study conducted by the American Chemical Society, water hardness across the United States varies greatly, with $CaCO_3$ concentration ranging from near zero for soft water to about 500 ppm $CaCO_3$ (about 200 ppm $Ca^{2+}$ ion) for very hard water. To ensure polymer formulation dispersibility across the country (and throughout the whole world), the ion-sensitive cationic polymer formulations of the present invention are desirably soluble in water containing up to about 50 ppm $Ca^{2+}$ and/or $Mg^{2+}$ ions. More desirably, the ion-sensitive cationic polymer formulations of the present invention are soluble in water containing up to about 100 ppm $Ca^{2+}$ and/or $Mg^{2+}$ ions. Even more desirably, the ion-sensitive cationic polymer formulations of the present invention are soluble in water containing up to about 150 ppm $Ca^{2+}$ and/or $Mg^{2+}$ ions. Even more desirably, the ion-sensitive cationic polymer formulations of the present invention are soluble in water containing up to about 200 ppm $Ca^{2+}$ and/or $Mg^{2+}$ ions.

Ion-Specific Cationic Polymer Compositions

The above-described ion-sensitive polymer compositions when used as a binder for woven or nonwoven substrates, such as wet wipes, helps maintain strength in the dry state, or in the wet state by ion triggerability. A high concentration of salt insolubilizes the binders and allows it to function as an adhesive for the web. This effect is referred to as "salting out." The above disclosures identify useful ion-sensitive polymer compositions as well as useful polymer/salt combinations, which allow for high strength in-use and under storage conditions, but allow the web to break apart in the toilet when the salt concentration falls below the critical level. As a part of the present invention, it has been discovered that a broader range of polymer composition may be useful in such triggerable applications, but the mechanism by which those compositions are rendered triggerable is mediated by the salt concentration and type. Thus, ion-specific trigger systems have been discovered that depend on the nature of the cationic polymer, the cationic species of the salt and the anionic species of the salt. In addition, it has been discovered that strength/dispersibility are closely mediated by both ion types. These new cationic polymer binder/salt combinations can be used to provide ion-specific trigger systems that are not only pH independent and relatively insensitive to water hardness, but function at much lower levels of added salt than the previous systems. As used herein, the ion-sensitive polymers and ion-specific polymers of the present invention will both be referred to as triggerable polymers.

The ion-specific cationic polymers of the present invention comprise 1) a cationic monomer, 2) at least one water insoluble, hydrophobic monomer, and optionally, 3) a hydrophilic and/or water-soluble nonionic monomer. The cationic monomers useful in the present invention include quaternary ammonium monomers, including, but not limited to, cationic monomer is selected from [2-(methacryloyloxy) ethyl] trimethyl ammonium chloride, (3-acrylamidopropyl)

trimethylammonium chloride, N,N-diallyldimethylammonium chloride, acryloxyethyltrimethyl ammonium chloride, acryloxyethyldimethylbenzyl ammonium chloride, methacryloxyethyldimethyl ammonium chloride, methacryloxyethyltrimethylbenzyl ammonium chloride and quaternized vinyl pyridine. Other vinyl functional monomers which when copolymerized with a water insoluble hydrophobic monomer form ionomers in the presence of divalent metal complex anions are also useful in the present invention.

The water insoluble hydrophobic monomers useful in the present invention include n-butyl acrylate and 2-ethylhexyl acrylate. Other n-alkyl or branched alkyl, acrylamido, acrylic esters and other vinyl functional monomers which when copolymerized with the cationic monomer form ionomers or ionomer-like structures in the presence of divalent metal complex anions are also useful in the present invention.

The hydrophilic and/or water-soluble nonionic monomer useful in the present invention include (meth)-acrylamide, substituted (meth)acrylamides, such as diacetone acrylamide, hydroxyalkyl (meth)-acrylate, hydroxyalkyl acrylates, such as hydroxyethyl acrylate or hydroxyethyl methacrylate (HEMA); polyethyleneglycol acrylates, polyethyleneglycol methacrylates, and vinyl pyrrolidone. Other vinyl functional monomers which when copolymerized with the water insoluble hydrophobic monomer and the cationic monomer form ionomers in the presence of divalent metal complex anions are also useful in the present invention.

The key to developing a successful ion-specific cationic polymer binder is to control the balance of the hydrophilic and hydrophobic monomers through a careful study of varying polymer compositions. Also, examination and observation of the binder's performance with specific cation and anion types as shown in the examples below has lead to the development of a proposed mechanism. Without wanting to be limited in any way by the proposed mechanism, applicants believe that the ion-specific polymer compositions of the present invention operate as follows. These results shown below indicate "ion specific" interactions rather than the "salting-out" effect seen in previous systems. Although ionic strength may play a role, the data presented here clearly indicates a new type of trigger mechanism based on hydrophobic associations and ion-specific interactions. The nature of this mechanism has been poorly understood until recently. It is believed that certain divalent metal ions, such as $Zn^{2+}$, $Ca^{2+}$ and $Mg^{2+}$, form complex ions in solution with halogen anions, such as $(ZnCl_4)^{2-}$ (F. Albert Cotton and Geoffrey William, *Advanced Inorganic Chemistry*, John Wiley and Sons. 1980). These complex ions have been isolated as the salts of large cations, such as quaternary ammonium ions. In addition, these interactions may become stronger in media of low dielectric constants. $Ca^{2+}$ and $Mg^{2+}$, do not typically form complexes in water, but do so in lower ketones and alcohols (i.e., at lower dielectric constant).

Therefore, it is believed the mechanism relies upon divalent metal ions that may form complex anions in the presence of the quaternary ammonium groups of the cationic co- and terpolymers. It is believed that these complex ions may "bridge" quaternary ammonium groups on the same polymer molecule or on other molecules and lead to a psuedo-crosslinked structure. Additionally, it is believed that these complex ion clusters organize into ionomer or ionomer-like domains, giving an overall morphology that results in good web strength in relatively low salt concentrations. Since the formation of the complex anions is highly dependant on the metal and counterion concentrations, the web become re-dispersible upon dilution with water that may contain other ions, even relatively high concentrations of other ions, such as found in hard water.

For the ion-specific copolymer made from a cationic monomer and a water insoluble, hydrophobic monomer, the mole percent of monomer in the copolymer is as follows: about 10 to less than 50 mole percent cationic monomer; and greater than 50 to about 90 mole percent water insoluble, hydrophobic monomer. More specifically, the mole percent of monomers in the copolymer is from about 15 to about 25 mole percent cationic monomer; and from about 70 to about 85 mole percent water insoluble, hydrophobic monomer. Most specifically, the mole percent of monomers in the copolymer is from about 20 mole percent cationic monomer; and about 80 mole percent water insoluble, hydrophobic monomer.

For the ion-specific terpolymer made from a cationic polymer, a water insoluble hydrophobic monomer and a water soluble or hydrophilic monomer, the mole percent of monomer in the terpolymer is as follows: about 5 to less than 50 mole percent cationic monomer; from about 30 to about 90 mole percent water insoluble hydrophobic monomer; and from about 10 to about 60 mole percent water soluble or hydrophilic monomer.

The ion-specific copolymers and terpolymers of the present invention may have an average molecular weight, which varies depending on the ultimate use of the polymer. The copolymers and terpolymers of the present invention have a weight average molecular weight ranging from about 10,000 to about 5,000,000. More specifically, the copolymers and terpolymers of the present invention have a weight average molecular weight ranging from about 25,000 to about 2,000,000, or, more specifically still, from about 200,000 to about 1,000,000.

The ion-specific copolymers and terpolymers of the present invention may be prepared according to the same free radical polymerization methods described above for the ion-sensitive cationic polymer.

As stated above, the mechanism of the ion-specific cationic polymer relies upon the interaction of the polymer cation and the amount and specific type of anion in a wetting solution. It has been discovered as a part of the present invention that the anion must be a divalent metal ion that forms a complex anion. Furthermore, the counterion of the divalent metal ion also seems to plays a role in the operability of the present invention. The divalent metal ions that are useful in the present invention include $Zn^{2+}$, $Ca^{2+}$ and $Mg^{2+}$. The counter ion for the divalent metal ion that are useful in the present invention include halogen ion, particularly $Cl^-$, $Br^-$ and $I^-$. Thus, salts that are useful in the present invention include $ZnCl_2$, $MgCl_2$, and $CaCl_2$. Other divalent metal salts that form complex anions in the presence of the quaternary ammonium group of the cationic polymer are also useful in the present invention.

Again, without wishing to be bound by a proposed mechanism, it appears that certain divalent ions, such as $Zn^{2+}$, may form complex ions in solution with halogen anions, such as $(ZnCl_4)^{2-}$ (F. Albert Cotton and Geoffrey William, *Advanced Inorganic Chemistry*, John Wiley and Sons. 1980). These complex ions have been isolated as the salts of large cations, such as quaternary ammonium ions. In addition, these interactions may become stronger in media of low dielectric constants. $Ca^{2+}$ and $Mg^{2+}$, do not typically form complexes in water, but do so in lower ketones and alcohols (i.e., at lower dielectric constant).

Therefore, the mechanism is believed to involve divalent metal ions that form complex anions in the presence of the quaternary ammonium groups of the co- and terpolymers. It is believed that these complex ions "bridge" quaternary ammonium groups on the same polymer molecule or on other molecules and lead to a psuedo-crosslinked structure. Additionally, it is believed that these complex ion clusters organized into ionomers, giving an overall morphology that results in good web strength in solutions containing specific amounts and types of salts. Since the formation of the complex anions is highly dependant on the metal and counterion concentrations, the web become re-dispersible upon dilution with water that does not contain the critical amount of these complex anions, but may contain other mono or divalent ions, such as found in hard or soft water.

In a further embodiment of the present invention, the above-described ion-specific cationic polymer formulations are used as binder materials for flushable and/or non-flushable products. In order to be effective as a binder material in flushable products throughout the United States, the ion-specific cationic polymer formulations of the present invention remain stable and maintain their integrity while dry or in relatively high concentrations of ions, but become soluble in water containing up to about 200 ppm or more divalent ions, especially calcium, magnesium and sulfonate ions. Desirably, the ion-specific cationic polymer formulations of the present invention are insoluble in a solution containing at least about 0.5 weight percent of one or more divalent metal salts capable of forming complex anions. More desirably, the ion-specific cationic polymer formulations of the present invention are insoluble in a solution containing from about 1 weight percent to about 5 weight percent of one or more divalent metal salts capable of forming complex anions. Even more desirably, the ion-specific cationic polymer formulations of the present invention are insoluble in solutions containing from about 2 weight percent to about 4 weight percent of one or more divalent metal salts capable of forming complex anions.

To ensure polymer formulation dispersibility across the country (and throughout the whole world), the ion-specific cationic polymer formulations of the present invention are desirably soluble in water containing up to about 50 ppm $Ca^{2+}$ and/or $Mg^{2+}$ ions. More desirably, the ion-specific cationic polymer formulations of the present invention are soluble in water containing up to about 100 ppm $Ca^{2+}$ and/or $Mg^{2+}$ ions. Even more desirably, the ion-specific cationic polymer formulations of the present invention are soluble in water containing up to about 150 ppm $Ca^{2+}$ and/or $Mg^{2+}$ ions. Even more desirably, the ion-specific cationic polymer formulations of the present invention are soluble in water containing up to about 200 ppm $Ca^{2+}$ and/or $Mg^{2+}$ ions.

Co-Binder Polymers

As stated above, the cationic polymer formulations of the present invention are formed from a single triggerable polymer or a combination of two or more different polymers, wherein at least one polymer is a triggerable polymer. The second polymer may be a co-binder polymer. A co-binder polymer is of a type and in an amount such that when combined with the triggerable polymer, the co-binder polymer desirably is largely dispersed in the triggerable polymer; i.e., the triggerable polymer is desirably the continuous phase and the co-binder polymer is desirably the discontinuous phase. Desirably, the co-binder polymer can also meet several additional criteria. For example, the co-binder polymer can have a glass transition temperature; i.e., $T_g$, that is lower than the glass transition temperature of the triggerable polymer. Furthermore or alternatively, the co-binder polymer can be insoluble in water, or can reduce the shear viscosity of the triggerable polymer. The co-binder can be present at a level relative to the solids mass of the triggerable polymer of about 45% or less, specifically about 30% or less, more specifically about 20% or less, more specifically still about 15% or less, and most specifically about 10% or less, with exemplary ranges of from about 1% to about 45% or from about 25% to about 35%, as well as from about 1% to about 20% or from about 5% to about 25%. The amount of co-binder present should be low enough, for co-binders with the potential to form water insoluble bonds or films, that the co-binder remains a discontinuous phase unable to create enough crosslinked, or insoluble bonds, to jeopardize the dispersibility of the treated substrate. In one embodiment, the polymer formulation of the present invention can comprise about 75 weight percent triggerable polymer and about 25 weight percent co-binder.

Desirably, but not necessarily, the co-binder polymer when combined with the triggerable polymer will reduce the shear viscosity of the triggerable polymer to such an extent that the combination of the triggerable polymer and the co-binder polymer is sprayable. By sprayable is meant that the polymer can be applied to a nonwoven fibrous substrate by spraying and the distribution of the polymer across the substrate and the penetration of the polymer into the substrate are such that the polymer formulation is uniformly applied to the substrate.

The co-binder polymer can be in the form of an emulsion latex. The surfactant system used in such a latex emulsion should be such that it does not substantially interfere with the dispersibility of the triggerable polymer.

In some embodiments, the combination of the triggerable polymer and the co-binder polymer reduces the stiffness of the article to which it is applied compared to the article with just the triggerable polymer. It has been found that when the triggerable polymer is applied to a nonwoven substrate, such as an air laid layer of wood pulp, for the purpose of forming a wet wipe, the nonwoven sheet can have an undesirable amount of stiffness that is detrimental to the dry product feel or to the handling of the dry web during processing, when the brittleness of the dry substrate can harm runnability. By combining the triggerable polymer and the co-binder polymer, the stiffness of such articles can be reduced.

The co-binder polymer of the present invention can have an average molecular weight, which varies depending on the ultimate use of the polymer. Desirably, the co-binder polymer has a weight average molecular weight ranging from about 500,000 to about 200,000,000. More desirably, the co-binder polymer has a weight average molecular weight ranging from about 500,000 to about 100,000,000.

Co-binder polymers that can meet many or all of the foregoing criteria include, but are not limited to, poly (ethylene-vinyl acetate), poly(styrene-butadiene), poly (styrene-acrylic), a vinyl acrylic terpolymer, neoprene, a polyester latex, an acrylic emulsion latex, poly vinyl chloride, ethylene-vinyl chloride copolymer, a carboxylated vinyl acetate latex, and the like, all of which can be non-crosslinking (e.g., devoid of N-methylol acrylamide or other crosslinkers), crosslinking, or potentially crosslinking (i.e., prepared with a crosslinker present) but not substantially crosslinked in the final product.

A particularly preferred non-crosslinking poly(ethylene-vinyl acetate) is Dur-O-Set® RB available from National Starch and Chemical Co., Bridgewater, N.J. A particularly preferred non-crosslinking poly(styrene-butadiene) is Rovene® 4817 available from Mallard Creek Polymers, Charlotte, N.C. A particularly preferred non-crosslinking poly(styrene-acrylic) is Rhoplex® NM 1715K available from Rohm and Haas, Philadelphia, Pa.

When a latex co-binder, or any potentially crosslinkable co-binder is used, the latex should be prevented from forming substantial water-insoluble bonds that bind the fibrous substrate together and interfere with the dispersibility of the article. Thus, the latex can be free of crosslinking agents, such as NMA, or free of catalyst for the crosslinker, or both. Alternatively, an inhibitor can be added that interferes with the crosslinker or with the catalyst such that crosslinking is impaired even when the article is heated to normal crosslinking temperatures. Such inhibitors can include free radical scavengers, methyl hydroquinone, t-butylcatechol, pH control agents such as potassium hydroxide, and the like. For some latex crosslinkers, such as N-methylol-acrylamide (NMA), for example, elevated pH such as a pH of 8 or higher can interfere with crosslinking at normal crosslinking temperatures (e.g., about 130° C. or higher). Also alternatively, an article comprising a latex co-binder can be maintained at temperatures below the temperature range at which crosslinking takes place, such that the presence of a crosslinker does not lead to crosslinking, or such that the degree of crosslinking remains sufficiently low that the dispersibility of the article is not jeopardized. Also alternatively, the amount of crosslinkable latex can be kept below a threshold level such that even with crosslinking, the article remains dispersible. For example, a small quantity of crosslinkable latex dispersed as discrete particles in an ion-sensitive binder can permit dispersibility even when fully crosslinked. For the later embodiment, the amount of latex can be below about 20 weight percent, and, more specifically, below about 15 weight percent relative to the ion-sensitive binder.

Latex compounds, whether crosslinkable or not, need not be the co-binder. SEM micrography of successful ion-sensitive binder films with useful non-crosslinking latex emulsions dispersed therein has shown that the latex co-binder particles can remain as discrete entities in the ion-sensitive binder, possibly serving in part as filler material. It is believed that other materials could serve a similar role, including a dispersed mineral or particulate filler in the triggerable binder, optionally comprising added surfactants/dispersants. For example, in one envisioned embodiment, freeflowing Ganzpearl PS-8F particles from Presperse, Inc. (Piscataway, N.J.), a styrene/divinylbenzene copolymer with about 0.4 micron particles, can be dispersed in a triggerable binder at a level of about 2 to 10 weight percent to modify the mechanical, tactile, and optical properties of the triggerable binder. Other filler-like approaches may include microparticles, microspheres, or microbeads of metal, glass, carbon, mineral, quartz, and/or plastic, such as acrylic or phenolic, and hollow particles having inert gaseous atmospheres sealed within their interiors. Examples include EXPANCEL phenolic microspheres from Expancel of Sweden, which expand substantially when heated, or the acrylic microspheres known as PM 6545 available from PQ Corporation of Pennsylvania. Foaming agents, including $CO_2$ dissolved in the triggerable binder, could also provide helpful discontinuities as gas bubbles in the matrix of an triggerable binder, allowing the dispersed gas phase in the triggerable binder to serve as the co-binder. In general, any compatible material that is not miscible with the binder, especially one with adhesive or binding properties of its own, can be used as the co-binder, if it is not provided in a state that imparts substantial covalent bonds joining fibers in a way that interferes with the water-dispersibility of the product. However, those materials that also provide additional benefits, such as reduced spray viscosity, can be especially preferred. Adhesive co-binders, such as latex that do not contain crosslinkers or contain reduced amounts of crosslinkers, have been found to be especially helpful in providing good results over a wide range of processing conditions, including drying at elevated temperatures.

As stated above, the $T_g$ of the co-binder polymer can be lower than the $T_g$ of the triggerable polymer, which is believed to improve the flexibility of the treated substrate, especially in the dry state. In Table 1 shown below is a comparison of the glass transition temperature of some of the preferred polymers useful in the present invention.

TABLE 1

Glass Transition Temperatures For Select Polymers

| Polymer | Glass Transition Temperature - Tg |
| --- | --- |
| Cationic Sample #1 from Example 2 below | 15° C. |
| Cationic Sample #6 from Example 2 below | 24° C. |
| Rhoplex NW 1715K (dry) | -6° C. |
| Rovene 4817 (dry) | -4° C. |
| Elite 33 (dry) | -10° C. |
| Elite 22 (dry) | -15° C. |

In an alternate embodiment, the triggerable polymer formulations of the present invention comprises about 55 to about 95 weight percent triggerable polymer and about 5 to about 45 weight percent poly(ethylene-vinyl acetate). More desirably, the triggerable polymer formulations of the present invention comprises about 75 weight percent triggerable polymer and about 25 weight percent poly(ethylene-vinyl acetate).

As stated above, useful co-binder polymers can include a variety of commercial latex emulsions, including those selected from the Rovene® series (styrene butadiene lattices available from Mallard Creek Polymers of Charlotte, N.C.), the Rhoplex® latices of Rohm and Haas Company, and the Elite® latices of National Starch. Polymer emulsions or dispersions generally comprise small polymer particles, such as crosslinkable ethylene vinyl acetate copolymers, typically in spherical form, dispersed in water and stabilized with surface active ingredients, such as low molecular weight emulsifiers or high molecular weight protective colloids. Care must be taken in selecting the proper emulsion system so that the emulsion will not interact with the cationic binder to interfere with the trigger property.

These liquid binders can be applied to airlaid webs or other substrates by methods known in the art of binder treatment for nonwoven webs, including spray or foam application, flooded nip impregnation, curtain coating, etc., followed by drying. In general, a wide variety of latex compounds and other resins or emulsions can be considered, including vinyl acetate copolymer latices, such as 76 RES 7800 from Union Oil Chemicals Divisions and Duroset RB®, Resyn® 25-1103, Resyn® 25-1109, Resyn® 25-1119, and Resyn® 25-1189 from National Starch and Chemical Corporation, ethylene-vinyl acetate copolymer emulsions, such as Airflex® ethylene-vinylacetate from Air Products and Chemicals Inc., acrylic-vinyl acetate copolymer emulsions, such as Rhoplex® AR-74 from Rohm and Haas Company, Synthemul® 97-726 from Reichhold Chemicals Inc., Resyn® 25-1140, 25-1141, 25-1142, and Resyn-6820 from National Starch and Chemical Corporation, vinyl acrylic terpolymer latices, such as 76 RES 3103 from Union Oil Chemical Division, and Resyn® 251110 from National Starch and Chemical Corporation, acrylic emulsion latices, such as Rhoplex® B-15J, Rhoplex® P-376, Rhoplex®

TR-407, Rhoplex® E-940, Rhoplex® TR934, Rhoplex® TR-520, Rhoplex® HA-24, and Rhoplex® NW1825 from Rohm and Haas Company, and Hycar® 2600 X 322, Hycar® 2671, Hycar® 2679, Hycar® 26120, and Hycar® 2600 X347 from B. F. Goodrich Chemical Group, styrene-butadiene latices, such as 76 RES 4100 and 76 RES 8100 available from Union Oil Chemicals Division, Tylac® resin emulsion 68412, Tylac® resin emulsion 68-067, 68-319, 68-413, 68-500, 68-501, available from Reichhold Chemical Inc., and DL6672A, DL6663A, DL6638A, DL6626A, DL6620A, DL615A, DL617A, DL620A, DL640A, DL650A available from Dow Chemical Company; and rubber latices, such as neoprene available from Serva Biochemicals; polyester latices, such as Eastman AQ 29D available from Eastman Chemical Company; vinyl chloride latices, such as Geon® 352 from B. F. Goodrich Chemical Group; ethylene-vinyl chloride copolymer emulsions, such as Airflex® ethylene-vinyl chloride from Air Products and Chemicals; polyvinyl acetate homopolymer emulsions, such as Vinac® from Air Products and Chemicals; carboxylated vinyl acetate emulsion resins, such as Synthemul® synthetic resin emulsions 40-502, 40-503, and 97-664 from Reichhold Chemicals Inc. and Polyco® 2149, 2150, and 2171 from Rohm and Haas Company. Silicone emulsions and binders can also be considered.

The co-binder polymer can comprise surface active compounds that improve the wettability of the substrate after application of the binder mixture. Wettability of a dry substrate that has been treated with a triggerable polymer formulation can be a problem in some embodiments, because the hydrophobic portions of the triggerable polymer formulation can become selectively oriented toward the air phase during drying, creating a hydrophobic surface that can be difficult to wet when the wetting composition is later applied unless surfactants are added to the wetting composition. Surfactants, or other surface active ingredients, in co-binder polymers can improve the wettability of the dried substrate that has been treated with a triggerable polymer formulation. Surfactants in the co-binder polymer should not significantly interfere with the triggerable polymer formulation. Thus, the binder should maintain good integrity and tactile properties in the pre-moistened wipes with the surfactant present.

In one embodiment, an effective co-binder polymer replaces a portion of the triggerable polymer formulation and permits a given strength level to be achieved in a pre-moistened wipe with at least one of lower stiffness, better tactile properties (e.g., lubricity or smoothness), or reduced cost, relative to an otherwise identical pre-moistened wipe lacking the co-binder polymer and comprising the triggerable polymer formulation at a level sufficient to achieve the given tensile strength.

Other Co-Binder Polymers

The Dry Emulsion Powder (DEP) binders of Wacker Polymer Systems (Burghausen, Germany) such as the VIN-NEK® system of binders, can be applied in some embodiments of the present invention. These are redispersible, free flowing binder powders formed from liquid emulsions. Small polymer particles from a dispersion are provided in a protective matrix of water soluble protective colloids in the form of a powder particle. The surface of the powder particle is protected against caking by platelets of mineral crystals. As a result, polymer particles that once were in a liquid dispersion are now available in a free flowing, dry powder form that can be redispersed in water or turned into swollen, tacky particles by the addition of moisture. These particles can be applied in highloft nonwovens by depositing them with the fibers during the airlaid process, and then later adding 10% to 30% moisture to cause the particles to swell and adhere to the fibers. This can be called the "chewing gum effect," meaning that the dry, non-tacky fibers in the web become sticky like chewing gum once moistened. Good adhesion to polar surfaces and other surfaces is obtained. These binders are available as free flowing particles formed from latex emulsions that have been dried and treated with agents to prevent cohesion in the dry state. They can be entrained in air and deposited with fibers during the airlaid process, or can be applied to a substrate by electrostatic means, by direct contact, by gravity feed devices, and other means. They can be applied apart from the binder, either before or after the binder has been dried. Contact with moisture, either as liquid or steam, rehydrates the latex particles and causes them to swell and to adhere to the fibers. Drying and heating to elevated temperatures (e.g., above 160° C.) causes the binder particles to become crosslinked and water resistant, but drying at lower temperatures (e.g., at 110° C. or less) can result in film formation and a degree of fiber binding without seriously impairing the water dispersibility of the pre-moistened wipes. Thus, it is believed that the commercial product can be used without reducing the amount of crosslinker by controlling the curing of the co-binder polymer, such as limiting the time and temperature of drying to provide a degree of bonding without significant crosslinking.

As pointed out by Dr. Klaus Kohlhammer in "New Airlaid Binders," *Nonwovens Report International*, September 1999, issue 342, pp. 20–22, 28–31, dry emulsion binder powders have the advantage that they can easily be incorporated into a nonwoven or airlaid web during formation of the web, as opposed to applying the material to an existing substrate, permitting increased control over placement of the co-binder polymer. Thus, a nonwoven or airlaid web can be prepared already having dry emulsion binders therein, followed by moistening when the ion-sensitive polymer formulation solution is applied, whereupon the dry emulsion powder becomes tacky and contributes to binding of the substrate. Alternatively, the dry emulsion powder can be entrapped in the substrate by a filtration mechanism after the substrate has been treated with triggerable binder and dried, whereupon the dry emulsion powder is rendered tacky upon application of the wetting composition.

In another embodiment, the dry emulsion powder is dispersed into the triggerable polymer formulation solution either by application of the powder as the triggerable polymer formulation solution is being sprayed onto the web or by adding and dispersing the dry emulsion powder particles into the triggerable polymer formulation solution, after which the mixture is applied to a web by spraying, by foam application methods, or by other techniques known in the art.

Binder Formulations and Fabrics Containing the Same

The triggerable polymer formulations of the present invention may be used as binders. The triggerable binder formulations of the present invention may be applied to any fibrous substrate. The binders are particularly suitable for use in water-dispersible products. Suitable fibrous substrates include, but are not limited to, nonwoven and woven fabrics. In many embodiments, particularly personal care products, preferred substrates are nonwoven fabrics. As used herein, the term "nonwoven fabric" refers to a fabric that has a structure of individual fibers or filaments randomly arranged in a mat-like fashion (including papers). Nonwoven fabrics can be made from a variety of processes including, but not limited to, air-laid processes, wet-laid processes, hydroentangling processes, staple fiber carding and bonding, and solution spinning.

The triggerable binder composition may be applied to the fibrous substrate by any known process of application. Suitable processes for applying the binder material include, but are not limited to, printing, spraying, electrostatic spraying, coating, flooded nips, metered press rolls, impregnating or by any other technique. The amount of binder composition may be metered and distributed uniformly within the fibrous substrate or may be non-uniformly distributed within the fibrous substrate. The binder composition may be distributed throughout the entire fibrous substrate or it may be distributed within a multiplicity of small closely spaced areas. In most embodiments, uniform distribution of binder composition is desired.

For ease of application to the fibrous substrate, the triggerable binder may be dissolved in water, or in a non-aqueous solvent, such as methanol, ethanol, acetone, or the like, with water being the preferred solvent. The amount of binder dissolved in the solvent may vary depending on the polymer used and the fabric application. Desirably, the binder solution contains up to about 50 percent by weight of binder composition solids. More desirably, the binder solution contains from about 10 to 30 percent by weight of binder composition solids, especially about 15–25 percent by weight binder composition solids. Plasticizers, perfumes, coloring agents, antifoams, bactericides, preservative, surface active agents, thickening agents, fillers, opacifiers, tackifiers, detackifiers, and similar additives can be incorporated into the solution of binder components, if so desired.

Once the triggerable binder composition is applied to the substrate, the substrate is dried by any conventional means. Once dry, the coherent fibrous substrate exhibits improved tensile strength when compared to the tensile strength of the untreated wet-laid or dry-laid substrates, and yet has the ability to rapidly "fall apart", or disintegrate when placed in soft or hard water having a relatively high multivalent ionic concentration and agitated. For example, the dry tensile strength of the fibrous substrate may be increased by at least 25 percent as compared to the dry tensile strength of the untreated substrate not containing the binder. More particularly, the dry tensile strength of the fibrous substrate may be increase by at least 100 percent as compared to the dry tensile strength of the untreated substrate not containing the binder. Even more particularly, the dry tensile strength of the fibrous substrate may be increased by at least 500 percent as compared to the dry tensile strength of the untreated substrate not containing the binder.

A desirable feature of the present invention is that the improvement in tensile strength is effected where the amount of binder composition present, "add-on", in the resultant fibrous substrate represents only a small portion by weight of the entire substrate. The amount of "add-on" can vary for a particular application; however, the optimum amount of "add-on" results in a fibrous substrate which has integrity while in use and also quickly disperses when agitated in water. For example, the binder components typically are from about 5 to about 65 percent, by weight, of the total weight of the substrate. More particularly, the binder components may be from about 10 to about 35 percent, by weight, of the total weight of the substrate. Even more particularly, the binder components may be from about 17 to about 22 percent by weight of the total weight of the substrate.

The nonwoven fabrics of the present invention have good in-use tensile strength, as well as, ion triggerability. Desirably, the nonwoven fabrics of the present invention are abrasion resistant and retain significant tensile strength in aqueous solutions containing the specific amount and type of ions disclosed above. Because of this latter property, nonwoven fabrics of the present invention are well suited for disposable products, such as sanitary napkins, diapers, adult incontinence products, and dry and premoistened wipes (wet wipes), which can be thrown in a flush toilet after use in any part of the world.

The fibers forming the fabrics above can be made from a variety of materials including natural fibers, synthetic fibers, and combinations thereof. The choice of fibers depends upon, for example, the intended end use of the finished fabric and fiber cost. For instance, suitable fibrous substrates may include, but are not limited to, natural fibers such as cotton, linen, jute, hemp, wool, wood pulp, etc. Similarly, regenerated cellulosic fibers, such as viscose rayon and cuprammonium rayon, modified cellulosic fibers, such as cellulose acetate, or synthetic fibers, such as those derived from polypropylenes, polyethylenes, polyolefins, polyesters, polyamides, polyacrylics, etc., alone or in combination with one another, may likewise be used. Blends of one or more of the above fibers may also be used, if so desired. Among wood pulp fibers, any known papermaking fibers may be used, including softwood and hardwood fibers. Fibers, for example, may be chemically pulped or mechanically pulped, bleached or unbleached, virgin or recycled, high yield or low yield, and the like. Mercerized, chemically stiffened or crosslinked fibers may also be used.

Synthetic cellulose fiber types include rayon in all its varieties and other fibers derived from viscose or chemically modified cellulose, including regenerated cellulose and solvent-spun cellulose, such as Lyocell. Chemically treated natural cellulosic fibers can be used, such as mercerized pulps, chemically stiffened or crosslinked fibers, or sulfonated fibers. Recycled fibers, as well as virgin fibers, can be used. Cellulose produced by microbes and other cellulosic derivatives can be used. As used herein, the term "cellulosic" is meant to include any material having cellulose as a major constituent, and, specifically, comprising at least 50 percent by weight cellulose or a cellulose derivative. Thus, the term includes cotton, typical wood pulps, non-woody cellulosic fibers, cellulose acetate, cellulose triacetate, rayon, thermomechanical wood pulp, chemical wood pulp, debonded chemical wood pulp, milkweed, or bacterial cellulose.

The triggerable binder of the present invention may also be applied to other fibers or particles. Other fibers that may be treated with the triggerable binder of the present invention such as fibers made from carboxymethyl cellulose, chitin, and chitiosan. The triggerable binder of the present invention may also be applied to particles, such as sodium polyacrylate super absorbent particles. Super absorbent particles are frequently incorporated on or into fibrous substrates used for personal care items, especially nonwoven fabrics.

The fiber length is important in producing the fabrics of the present invention. In some embodiments, such as flushable products, fiber length is of more importance. The minimum length of the fibers depends on the method selected for forming the fibrous substrate. For example, where the fibrous substrate is formed by carding, the length of the fiber should usually be at least about 42 mm in order to insure uniformity.

Where the fibrous substrate is formed by air-laid or wet-laid processes, the fiber length may desirably be about 0.2 to 6 mm. Although fibers having a length of greater than 50 mm are within the scope of the present invention, it has been determined that when a substantial quantity of fibers having a length greater than about 15 mm is placed in a flushable fabric, though the fibers will disperse and separate in water, their length tends to form "ropes" of fibers, which are undesirable when flushing in home toilets. Therefore, for these products, it is desired that the fiber length be about 15 mm or less so that the fibers will not have a tendency to "rope" when they are flushed through a toilet. Although fibers of various lengths are applicable in the present invention, desirably fibers are of a length less than about 15 mm so that the fibers disperse easily from one another when in contact with water. The fibers, particularly synthetic fibers, can also be crimped.

The fabrics of the present invention may be formed from a single layer or multiple layers. In the case of multiple layers, the layers are generally positioned in a juxtaposed or surface-to-surface relationship and all or a portion of the layers may be bound to adjacent layers. Nonwoven webs of the present invention may also be formed from a plurality of separate nonwoven webs wherein the separate nonwoven webs may be formed from single or multiple layers. In those instances where the nonwoven web includes multiple layers, the entire thickness of the nonwoven web may be subjected to a binder application or each individual layer may be separately subjected to a binder application and then combined with other layers in a juxtaposed relationship to form the finished nonwoven web.

In one embodiment, the fabric substrates of the present invention may be incorporated into cleansing and body fluid absorbent products, such as sanitary napkins, diapers, adult incontinence products, surgical dressings, tissues, wet wipes, and the like. These products may include an absorbent core, comprising one or more layers of an absorbent fibrous material. The core may also comprise one or more layers of a fluid-pervious element, such as fibrous tissue, gauze, plastic netting, etc. These are generally useful as wrapping materials to hold the components of the core together. Additionally, the core may comprise a fluid-impervious element or barrier means to preclude the passage of fluid through the core and on the outer surfaces of the product. Desirably, the barrier means also is water-dispersible. A film of a polymer having substantially the same composition as the aforesaid water-dispersible binder is particularly well-suited for this purpose. In accordance with the present invention, the polymer compositions are useful for forming each of the above-mentioned product components including the layers of absorbent core, the fluid-pervious element, the wrapping materials, and the fluid-impervious element or barrier means.

The triggerable binder formulations of the present invention are particularly useful for binding fibers of air-laid nonwoven fabrics. These air-laid materials are useful for body-side liners, fluid distribution materials, fluid in-take materials, such as a surge material, absorbent wrap sheet and cover stock for various water-dispersible personal care products. Air-laid materials are particularly useful for use as a pre-moistened wipe (wet wipe). The basis weights for air-laid non-woven fabrics may range from about 20 to about 200 grams per square meter ("gsm") with staple fibers having a denier of about 0.5–10 and a length of about 6–15 millimeters. Surge, or in-take, materials need better resiliency and higher loft so staple fibers having about 6 denier or greater are used to make these products. A desirable final density for the surge, or in-take, materials is between about 0.025 grams per cubic centimeter ("g/cc") to about 0.10 g/cc. Fluid distribution materials may have a higher density, in the desired range of about 0.10 to about 0.20 g/cc using fibers of lower denier, most desirable fibers have a denier of less than about 1.5. Wipes generally can have a fiber density of about 0.025 g/cc to about 0.2 g/cc and a basis weight of about 20 gsm to about 150 gsm; specifically from about 30 to about 90 gsm, and most specifically from about 60 gsm to about 65 gsm.

The nonwoven fabrics of the present invention may also be incorporated into such body fluid absorbing products as sanitary napkins, diapers, surgical dressings, tissues and the like. In one embodiment, the triggerable binder is such that it will not dissolve when contacted by body fluids since the concentration of monovalent ions in the body fluids is above the level needed for dissolution; i.e., greater than 2% by weight. The nonwoven fabric retains its structure, softness and exhibits a toughness satisfactory for practical use. However, when brought into contact with water having a concentration of multivalent ions, such as $Ca^{2+}$ and $Mg^{2+}$ ions, of up to about 200 ppm or more, the binder disperses. The nonwoven fabric structure is then easily broken and dispersed in the water.

In one embodiment of the present invention, the in-use tensile strength of a nonwoven fabric is enhanced by forming the nonwoven fabric with a binder material comprising the triggerable polymer formulation of the present invention and subsequently applying either one or more monovalent and/or multivalent salts to the nonwoven fabric or salts of divalent metal ions that form complex anions. The salt may be applied to the nonwoven fabric by any method known to those of ordinary skill in the art including, but not limited to, applying a solid powder onto the fabric and spraying a salt solution onto the fabric. The amount of salt may vary depending on a particular application. However, the amount of salt applied to the fabric is typically from about 0.5 weight percent to about 10 weight percent salt solids based on the total weight of the fabric. The salt-containing fabrics of the present invention may be used in a variety of fabric applications including, but not limited to, feminine pads, surgical dressings, and diapers.

Those skilled in the art will readily understand that the binder formulations and fibrous substrates of the present invention may be advantageously employed in the preparation of a wide variety of products, including but not limited to, absorbent personal care products designed to be contacted with body fluids. Such products may only comprise a single layer of the fibrous substrate, or may comprise a combination of elements, as described above. Although the binder formulations and fibrous substrates of the present invention are particularly suited for personal care products, the binder formulations and fibrous substrates may be advantageously employed in a wide variety of consumer products.

Unlike other binder systems known in the art, the triggerable polymer formulations of the present invention can be activated as binders without the need for elevated temperature. While drying or water removal is useful in achieving a good distribution of the binder in a fibrous web, elevated temperature, per se, is not essential because the binder does not require crosslinking or other chemical reactions with high activation energy to serve as a binder. Rather, the interaction with a soluble insolubilizing compound, typically a salt, is sufficient to cause the binder to become insoluble; i.e., "salted out" or activated by interaction between the cation of the polymer and the divalent metal complex anion from the salt. Thus, a drying step can be avoided, if desired, or replaced with low-temperature water removal operations such as room-temperature drying or freeze drying. Elevated temperature is generally helpful for drying, but the drying can be done at temperatures below what is normally needed to drive crosslinking reactions. Thus, the peak temperature to which the substrate is exposed or to which the substrate is brought can be below any of the following: 180° C., 160° C., 140° C., 120° C., 110° C., 105° C., 100° C., 90° C., 75° C., and 60° C., with an exemplary range for peak web temperature of from about 50° C. to about 110° C., or from about 70° C. to about 140° C. Of course, higher temperatures can be used, but are not necessary in most embodiments. While polymer systems, such as commercial latex emulsions, may also comprise crosslinkers suited for reaction at temperatures of 160° C. or higher, maintaining a lower peak temperature can be beneficial in preventing development of excessive strength in the polymer that might otherwise hinder the water dispersibility of the pre-moistened wipe.

Wet Wipe Wetting Composition and Wet Wipes Containing the Same

One particularly interesting embodiment of the present invention is the production of pre-moistened wipes, or wet wipes, from the above-described triggerable binder compositions and fibrous materials. For wipes, the fibrous material may be in the form of a woven or nonwoven fabric; however, nonwoven fabrics are more desirable. The nonwoven fabric is desirably formed from relatively short fibers, such as wood pulp fibers. The minimum length of the fibers depends on the method selected for forming the nonwoven fabric. Where the nonwoven fabric is formed by a wet or dry method, the fiber length is desirably from about 0.1 millimeters to 15 millimeters. Desirably, the nonwoven fabric of the present invention has a relatively low wet cohesive strength when it is not bonded together by an adhesive or binder material. When such nonwoven fabrics are bonded together by a binder composition, which loses its bonding strength in tap water and in sewer water, the fabric will break up readily by the agitation provided by flushing and moving through the sewer pipes.

The finished wipes may be individually packaged, desirably in a folded condition, in a moisture proof envelope or packaged in containers holding any desired number of sheets in a water-tight package with a wetting composition applied to the wipe. The finished wipes may also be packaged as a roll of separable sheets in a moisture-proof container holding any desired number of sheets on the roll with a wetting composition applied to the wipes. The roll can be coreless and either hollow or solid. Coreless rolls, including rolls with a hollow center or without a solid center, can be produced with known coreless roll winders, including those of SRP Industry, Inc. (San Jose, Calif.); Shimizu Manufacturing (Japan), and the devices disclosed in U.S. Pat. No. 4,667,890, issued May 26, 1987 to Gietman. Solid-wound coreless rolls can offer more product for a given volume and can be adapted for a wide variety of dispensers.

Relative to the weight of the dry fabric, the wipe may desirably contain from about 10 percent to about 400 percent of the wetting composition, more desirably from about 100 percent to about 300 percent of the wetting composition, and even more desirably from about 180 percent to about 240 percent of the wetting composition. The wipe maintains its desired characteristics over the time periods involved in warehousing, transportation, retail display and storage by the consumer. Accordingly, shelf life may range from two months to two years.

Various forms of impermeable envelopes and storage means for containing wet-packaged materials, such as wipes and towelettes and the like, are well known in the art. Any of these may be employed in packaging the pre-moistened wipes of the present invention.

Desirably, the pre-moistened wipes of the present invention are wetted with an aqueous wetting composition, which has one or more of the following properties:

(1) is compatible with the above-described triggerable binder compositions of the present invention;

(2) enables the pre-moistened wipe to maintain its wet strength during converting, storage and usage (including dispensing), as well as, dispersibility in a toilet bowl;

(3) does not cause skin irritation;

(4) reduces tackiness of the wipe, and provides unique tactile properties, such as skin glide and a "lotion-like feel"; and (5) acts as a vehicle to deliver "moist cleansing" and other skin health benefits.

The wetting composition should not act as a solvent for the binder and generally does not contain solvents other than water, and particularly does not contain organic solvents, though a small quantity (<1%) of a fragrance solubilizer, such as polysorbate 20, may be present, depending on the fragrance and the salt concentration of the wetting composition. Desirably, the wetting composition contains less than about 10 weight percent of organic solvents, such as propylene glycol or other glycols, polyhydroxy alcohols, and the like, based on the total weight of the wetting composition. More desirably, the wetting composition contains less than about 4 weight percent of organic solvents. Even more desirably, the wetting composition contains less than about 1 weight percent of organic solvents. The wetting composition can be substantially free of organic solvents. By substantially free is meant containing only a trivial or inconsequential amount, or an amount such that it has no effect on the triggerable property of the product.

One aspect of the present invention is a wetting composition, which contains an insolubilizing agent that maintains the strength of a water-dispersible binder until the insolubilizing agent is diluted with water, whereupon the strength of the water-dispersible binder begins to decay. The water-dispersible binder may be any of the triggerable binder compositions of the present invention or any other triggerable binder composition. The insolubilizing agent in the wetting composition can be a salt, such as those disclosed for the various triggerable polymers, a blend of salts having both monovalent and multivalent ions, or any other compound, which provides in-use and storage strength to the water-dispersible binder composition, and can be diluted in water to permit dispersion of the substrate as the binder polymer triggers to a weaker state. Desirably, the wetting composition contains more than about 2 weight percent of an insolubilizing agent based on the total weight of the wetting composition for ion-sensitive polymers and more than about 0.5 weight percent of an insolubilizing agent based on the total weight of the wetting composition for ion-specific polymers. Specifically, the wetting composition may contain from about 0.5 weight percent to about 20 weight percent of an insolubilizing agent insolubilizing agent. Even more specifically, the wetting composition may contain from about 1 weight percent to about 5 weight percent of an insolubilizing agent. More precisely, the wetting composition may contain from about 2 weight percent to about 4 weight percent of an insolubilizing agent. A preferred blend of salts is NaCl and $ZnCl_2$.

The wetting composition of the present invention may further comprise a variety of additives compatible with the insolubilizing agent and the water-dispersible binder, such that the strength and dispersibility functions of the wipe are not jeopardized. Suitable additives in the wetting composition include, but are not limited to, the following additives:

skin-care additives; odor control agents; detackifying agents to reduce the tackiness of the binder; particulates; antimicrobial agents; preservatives; wetting agents and cleaning agents, such as detergents, surfactants, some silicones; emollients; surface feel modifiers for improved tactile sensation (e.g., lubricity) on the skin; fragrance; fragrance solubilizers; opacifiers; fluorescent whitening agents; UV absorbers; pharmaceuticals; and pH control agents, such as malic acid or potassium hydroxide.

Skin-Care Additives

As used herein, the term "skin-care additives" represents additives, which provide one or more benefits to the user, such as a reduction in the probability of having diaper rash and/or other skin damage caused by fecal enzymes. These enzymes, particularly trypsin, chymotrypsin and elastase, are proteolytic enzymes produced in the gastrointestinal tract to digest food. In infants, for example, the feces tend to be watery and contain, among other materials, bacteria, and some amounts of undegraded digestive enzymes. These enzymes, if they remain in contact with the skin for any appreciable period of time, have been found to cause an irritation that is uncomfortable in itself and can predispose the skin to infection by microorganisms. As a countermeasure, skin-care additives include, but are not limited to, the enzyme inhibitors and sequestrants set forth hereafter. The wetting composition may contain less than about 5 weight percent of skin-care additives based on the total weight of the wetting composition. More specifically, the wetting composition may contain from about 0.01 weight percent to about 2 weight percent of skin-care additives. Even more specifically, the wetting composition may contain from about 0.01 weight percent to about 0.05 weight percent of skin-care additives.

A variety of skin-care additives may be added to the wetting composition and the pre-moistened wipes of the present invention or included therein. In one embodiment of the present invention, skin-care additives in the form of particles are added to serve as fecal enzyme inhibitors, offering potential benefits in the reduction of diaper rash and skin damage caused by fecal enzymes. U.S. Pat. No. 6,051, 749, issued Apr. 18, 2000 to Schulz et al., the entirety of which is herein incorporated by reference, discloses organophilic clays in a woven or nonwoven web, said to be useful for inhibiting fecal enzymes. Such materials may be used in the present invention, including reaction products of a long chain organic quaternary ammonium compound with one or more of the following clays: montmorillonite, bentonite, beidellite, hectorite, saponite, and stevensite.

Other known enzyme inhibitors and sequestrants may be used as skin-care additives in the wetting composition of the present invention, including those that inhibit trypsin and other digestive or fecal enzymes, and inhibitors for urease. For example, enzyme inhibitors and anti-microbial agents may be used to prevent the formation of odors in body fluids. For example, urease inhibitors, which are also said to play a role in odor absorption, are disclosed by T. Trinh in World Patent Application No. 98/26808, "Absorbent Articles with Odor Control System," published Jun. 25, 1998, the entirety of which is herein incorporated by reference. Such inhibitors may be incorporated into the wetting composition and the pre-moistened wipes of the present invention and include transition metal ions and their soluble salts, such as silver, copper, zinc, ferric, and aluminum salts. The anion may also provide urease inhibition, such as borate, phytate, etc. Compounds of potential value include, but are not limited to, silver chlorate, silver nitrate, mercury acetate, mercury chloride, mercury nitrate, copper metaborate, copper bromate, copper bromide, copper chloride, copper dichromate, copper nitrate, copper salicylate, copper sulfate, zinc acetate, zinc borate, zinc phytate, zinc bromate, zinc bromide, zinc chlorate, zinc chloride, zinc sulfate, cadmium acetate, cadmium borate, cadmium bromide, cadmium chlorate, cadmium chloride, cadmium formate, cadmium iodate, cadmium iodide, cadmium permanganate, cadmium nitrate, cadmium sulfate, and gold chloride.

Other salts that have been disclosed as having urease inhibition properties include ferric and aluminum salts, especially the nitrates, and bismuth salts. Other urease inhibitors are disclosed by Trinh, including hydroxamic acid and its derivatives; thiourea; hydroxylamine; salts of phytic acid; extracts of plants of various species, including various tannins, e.g. carob tannin, and their derivatives such as chlorogenic acid derivatives; naturally occurring acids such as ascorbic acid, citric acid, and their salts; phenyl phosphoro diamidate/diamino phosphoric acid phenyl ester; metal aryl phosphoramidate complexes, including substituted phosphorodiamidate compounds; phosphoramidates without substitution on the nitrogen; boric acid and/or its salts, including especially, borax, and/or organic boron acid compounds; the compounds disclosed in European Patent Application 408,199; sodium, copper, manganese, and/or zinc dithiocarbamate; quinones; phenols; thiurams; substituted rhodanine acetic acids; alkylated benzoquinones; formamidine disulphide; 1:3-diketones maleic anhydride; succinamide; phthalic anhydride; pehenic acid; /N,N-dihalo-2-imidazolidinones; N-halo2-oxazolidinones; thio- and/or acyl-phosphoryltnamide and/or substituted derivatives thereof-, thiopyridine-N-oxides, thiopyridines, and thiopyrimidines; oxidized sulfur derivatives of diaminophosphinyl compounds; cyclotriphosphazatriene derivatives; ortho-diaminophosphinyl derivatives of oximes; bromo-nitro compounds; S-aryl and/or alkyl diamidophosphorothiolates; diaminophosphinyl derivatives; mono- and/or polyphosphorodiamide; 5-substituted-benzoxathiol-2-ones; N(diaminophosphinyl)arylcarboxamides; alkoxy-1,2-benzothaizin compounds; etc.

Many other skin-care additives may be incorporated into the wetting composition and pre-moistened wipes of the present invention, including, but not limited to, sun blocking agents and UV absorbers, acne treatments, pharmaceuticals, baking soda (including encapsulated forms thereof), vitamins and their derivatives such as Vitamins A or E, botanicals such as witch hazel extract and aloe vera, allantoin, emollients, disinfectants, hydroxy acids for wrinkle control or anti-aging effects, sunscreens, tanning promoters, skin lighteners, deodorants and antiperspirants, ceramides for skin benefits and other uses, astringents, moisturizers, nail polish removers, insect repellants, antioxidants, antiseptics, anti-inflammatory agents and the like, provided that the additives are compatible with an ion-sensitive binder composition associated therewith, and especially the ion-sensitive binder compositions of the present invention (i.e., they do not cause a substantial loss of strength in the wet state of the pre-moistened wipes, prior to dilution in water, while permitting dispersibility in water).

Useful materials for skin care and other benefits are listed in *McCutcheon's* 1999, Vol. 2: Functional Materials, MC Publishing Company, Glen Rock, N.J. Many useful botanicals for skin care are provided by Active Organics, Lewisville, Tex.

Odor Control Additives

Suitable odor control additives for use in the wetting composition and pre-moistened wipes of the present invention include, but are not limited to, zinc salts; talc powder;

encapsulated perfumes (including microcapsules, macrocapsules, and perfume encapsulated in liposomes, vessicles, or microemulsions); chelants, such as ethylenediamine tetra-acetic acid; zeolites; activated silica, activated carbon granules or fibers; activated silica particulates; polycarboxylic acids, such as citric acid; cyclodextrins and cyclodextrin derivatives; chitosan or chitin and derivatives thereof; oxidizing agents; antimicrobial agents, including silver-loaded zeolites (e.g., those of BF Technologies, located in Beverly, Mass., sold under the trademark HEALTHSHIELD™); triclosan; kieselguhr; and mixtures thereof. In addition to controlling odor from the body or body wastes, odor control strategies can also be employed to mask or control any odor of the treated substrate. Desirably, the wetting composition contains less than about 5 weight percent of odor control additives based on the total weight of the wetting composition. More desirably, the wetting composition contains from about 0.01 weight percent to about 2 weight percent of odor control additives. Even more desirably, the wetting composition contains from about 0.03 weight percent to about 1 weight percent of odor control additives.

In one embodiment of the present invention, the wetting composition and/or pre-moistened wipes comprise derivatized cyclodextrins, such as hydroxypropyl beta-cyclodextrin in solution, which remain on the skin after wiping and provide an odor-absorbing layer. In other embodiments, the odor source is removed or neutralized by application of an odor-control additive, exemplified by the action of a chelant that binds metal groups necessary for the function of many proteases and other enzymes that commonly produce an odor. Chelating the metal group interferes with the enzyme's action and decreases the risk of malodor in the product.

Principles for the application of chitosan or chitin derivatives to nonwoven webs and cellulosic fibers are described by S. Lee et al. in "Antimicrobial and Blood Repellent Finishes for Cotton and Nonwoven Fabrics Based on Chitosan and Fluoropolymers," Textile Research Journal, 69(2); 104–112, February 1999.

Detackifying Agents

While elevated salt concentrations may reduce the tack of the triggerable binder, other means of tack reduction are often desirable. Thus, detackifying agents may be used in the wetting composition to reduce the tackiness, if any, of the triggerable binder. Suitable detackifiers include any substance known in the art to reduce tack between two adjacent fibrous sheets treated with an adhesive-like polymer or any substance capable of reducing the tacky feel of an adhesive-like polymer on the skin. Detackifiers may be applied as solid particles in dry form, as a suspension or as a slurry of particles. Deposition may be by spray, coating, electrostatic deposition, impingement, filtration (i.e., a pressure differential drives a particle-laden gas phase through the substrate, depositing particles by a filtration mechanism), and the like, and may be applied uniformly on one or more surfaces of the substrate or may be applied in a pattern (e.g., repeating or random patterns) over a portion of the surface or surfaces of the substrate. The detackifier may be present throughout the thickness of the substrate, but may be concentrated at one or both surfaces, and may be substantially only present on one or both surfaces of the substrate.

Specific detackifiers include, but are not limited to, powders, such as talc powder, calcium carbonate, mica; starches, such as corn starch; lycopodium powder; mineral fillers, such as titanium dioxide; silica powder; alumina; metal oxides in general; baking powder; kieselguhr; and the like. Polymers and other additives having low surface energy may also be used, including a wide variety of fluorinated polymers, silicone additives, polyolefins and thermoplastics, waxes, debonding agents known in the paper industry including compounds having alkyl side chains such as those having 16 or more carbons, and the like. Compounds used as release agents for molds and candle making may also be considered, as well as, dry lubricants and fluorinated release agents.

In one embodiment, the detackifier comprises polytetrafluoroethylene (PTFE), such as PTFE telomer (KRYTOX® DF) compound, used in the PTFE release agent dry lubricant MS-122DF, marketed by Miller-Stephenson (Danbury, Conn.) as a spray product. For example, PTFE particles may be applied by spray to one side of the substrate prior to winding of the pre-moistened wipes. In one embodiment, a detackifying agent is applied to only one surface of the substrate prior to winding into a roll.

The wetting composition desirably contains less than about 25 weight percent of detackifying agents based on the total weight of the wetting composition. More desirably, the wetting composition contains from about 0.01 weight percent to about 10 weight percent of detackifying agents, more specifically about 5% or less. Even more specifically, the wetting composition contains from about 0.05 weight percent to about 2 weight percent of detackifying agents.

In addition to acting as a detackifying agent, starch compounds may also improve the strength properties of the pre-moistened wipes. For example, it has been found that ungelled starch particles, such as hydrophilic tapioca starch, when present at a level of about 1% or higher by weight relative to the weight of the wetting composition, can permit the pre-moistened wipe to maintain the same strength at a lower salt concentration than is possible without the presence of starch. Thus, for example, a given strength can be achieved with 2% salt in the wetting composition in the presence of salt compared to a level of 4% salt being needed without starch. Starch may be applied by adding the starch to a suspension of laponite to improve the dispersion of the starch within the wetting composition.

Microparticulates

The wetting composition of the present invention may be further modified by the addition of solid particulates or microparticulates. Suitable particulates include, but are not limited to, mica, silica, alumina, calcium carbonate, kaolin, talc, and zeolites. The particulates may be treated with stearic acid or other additives to enhance the attraction or bridging of the particulates to the binder system, if desired. Also, two-component microparticulate systems, commonly used as retention aids in the papermaking industry, may also be used. Such two-component microparticulate systems generally comprise a colloidal particle phase, such as silica particles, and a water-soluble cationic polymer for bridging the particles to the fibers of the web to be formed. The presence of particulates in the wetting composition can serve one or more useful functions, such as (1) increasing the opacity of the pre-moistened wipes; (2) modifying the rheology or reducing the tackiness of the pre-moistened wipe; (3) improving the tactile properties of the wipe; or (4) delivering desired agents to the skin via a particulate carrier, such as a porous carrier or a microcapsule. Desirably, the wetting composition contains less than about 25 weight percent of particulate based on the total weight of the wetting composition. More specifically, the wetting composition may contain from about 0.05 weight percent to about 10 weight percent of microparticulate. Even more specifically, the wetting composition may contain from about 0.1 weight percent to about 5 weight percent of microparticulate.

Microcapsules and other Delivery Vehicles

Microcapsules and other delivery vehicles may also be used in the wetting composition of the present invention to provide skin-care agents; medications; comfort promoting agents, such as eucalyptus; perfumes; skin care agents; odor control additives; vitamins; powders; and other additives to the skin of the user. Specifically, the wetting composition may contain up to about 25 weight percent of microcapsules or other delivery vehicles based on the total weight of the wetting composition. More specifically, the wetting composition may contain from about 0.05 weight percent to about 10 weight percent of microcapsules or other delivery vehicles. Even more specifically, the wetting composition may contain from about 0.2 weight percent to about 5.0 weight percent of microcapsules or other delivery vehicles.

Microcapsules and other delivery vehicles are well known in the art. For example, POLY-PORE® E200 (Chemdal Corp., Arlington Heights, Ill.), is a delivery agent comprising soft, hollow spheres that can contain an additive at over 10 times the weight of the delivery vehicle. Known additives reported to have been used with POLY-PORE® E200 include, but are not limited to, benzoyl peroxide, salicylic acid, retinol, retinyl palmitate, octyl methoxycinnamate, tocopherol, silicone compounds (DC 435), and mineral oil. Another useful delivery vehicle is a sponge-like material marketed as POLY-PORE® L200, which is reported to have been used with silicone (DC 435) and mineral oil. Other known delivery systems include cyclodextrins and their derivatives, liposomes, polymeric sponges, and spray-dried starch.

Additives present in microcapsules are isolated from the environment and the other agents in the wetting composition until the wipe is applied to the skin, whereupon the microcapsules break and deliver their load to the skin or other surfaces.

Preservatives and Anti-Microbial Agents

The wetting composition of the present invention may also contain preservatives and/or anti-microbial agents. Several preservatives and/or anti-microbial agents, such as Mackstat H 66 (available from McIntyre Group, Chicago, Ill.), have been found to give excellent results in preventing bacteria and mold growth. Other suitable preservatives and anti-microbial agents include, but are not limited to DMDM hydantoin (e.g., Glydant Plus™, Lonza, Inc., Fair Lawn, N.J.), iodopropynyl butylcarbamate, Kathon (Rohn and Hass, Philadelphia, Pa.), methylparaben, propylparaben, 2-bromo-2-nitropropane-1,3-diol, benzoic acid, and the like. Desirably, the wetting composition contains less than about 2 weight percent on an active basis of preservatives and/or anti-microbial agents based on the total weight of the wetting composition. More desirably, the wetting composition contains from about 0.01 weight percent to about 1 weight percent of preservatives and/or anti-microbial agents. Even more desirably, the wetting composition contains from about 0.01 weight percent to about 0.5 weight percent of preservatives and/or anti-microbial agents.

Wetting Agents and Cleaning Agents

A variety of wetting agents and/or cleaning agents may be used in the wetting composition of the present invention. Suitable wetting agents and/or cleaning agents include, but are not limited to, detergents and nonionic, amphoteric, and anionic surfactants, especially amino acid-based surfactants. Amino acid-based surfactant systems, such as those derived from amino acids L-glutamic acid and other natural fatty acids, offer pH compatibility to human skin and good cleansing power, while being relatively safe and providing improved tactile and moisturization properties compared to other anionic surfactants. One function of the surfactant is to improve wetting of the dry substrate with the wetting composition. Another function of the surfactant can be to disperse bathroom soils when the pre-moistened wipe contacts a soiled area and to enhance their absorption into the substrate. The surfactant can further assist in make-up removal, general personal cleansing, hard surface cleansing, odor control, and the like.

One commercial example of an amino-acid based surfactant is acylglutamate, marketed under the Amisoft name by Ajinomoto Corp., Tokyo, Japan. Desirably, the wetting composition contains less than about 3 weight percent of wetting agents and/or cleaning agents based on the total weight of the wetting composition. More desirably, the wetting composition contains from about 0.01 weight percent to about 2 weight percent of wetting agents and/or cleaning agents. Even more desirably, the wetting composition contains from about 0.1 weight percent to about 0.5 weight percent of wetting agents and/or cleaning agents.

Although amino-acid based surfactants are particularly useful in the wetting compositions of the present invention, a wide variety of surfactants may be used in the present invention. Suitable non-ionic surfactants include, but are not limited to, the condensation products of ethylene oxide with a hydrophobic (oleophilic) polyoxyalkylene base formed by the condensation of propylene oxide with propylene glycol. The hydrophobic portion of these compounds desirably has a molecular weight sufficiently high so as to render it water-insoluble. The addition of polyoxyethylene moieties to this hydrophobic portion increases the water-solubility of the molecule as a whole, and the liquid character of the product is retained up to the point where the polyoxyethylene content is about 50% of the total weight of the condensation product. Examples of compounds of this type include commercially-available Pluronic surfactants (BASF Wyandotte Corp.), especially those in which the polyoxypropylene ether has a molecular weight of about 1500–3000 and the polyoxyethylene content is about 35–55% of the molecule by weight, i.e. Pluronic L-62.

Other useful nonionic surfactants include, but are not limited to, the condensation products of $C_8$–$C_{22}$ alkyl alcohols with 2–50 moles of ethylene oxide per mole of alcohol. Examples of compounds of this type include the condensation products of $C_{11}$–$C_{15}$ secondary alkyl alcohols with 3–50 moles of ethylene oxide per mole of alcohol, which are commercially-available as the Poly-Tergent SLF series from Olin Chemicals or the TERGITOL® series from Union Carbide; i.e., TERGITOL® 25-L-7, which is formed by condensing about 7 moles of ethylene oxide with a $C_{12}$–$C_{15}$ alkanol.

Other nonionic surfactants, which may be employed in the wetting composition of the present invention, include the ethylene oxide esters of $C_6$–$C_{12}$ alkyl phenols such as (nonylphenoxy)polyoxyethylene ether. Particularly useful are the esters prepared by condensing about 8–12 moles of ethylene oxide with nonylphenol, i.e. the IGEPAL® CO series (GAF Corp.).

Further non-ionic surface active agents include, but are not limited to, alkyl polyglycosides (APG), derived as a condensation product of dextrose (D-glucose) and a straight or branched chain alcohol. The glycoside portion of the surfactant provides a hydrophile having high hydroxyl density, which enhances water solubility. Additionally, the inherent stability of the acetal linkage of the glycoside provides chemical stability in alkaline systems.

Furthermore, unlike some non-ionic surface active agents, alkyl polyglycosides have no cloud point, allowing one to formulate without a hydrotrope, and these are very mild, as well as readily biodegradable non-ionic surfactants. This class of surfactants is available from Horizon Chemical under the trade names of APG-300, APG-350, APG-500, and APG-500.

Silicones are another class of wetting agents available in pure form, or as microemulsions, macroemulsions, and the like. One exemplary non-ionic surfactant group is the silicone-glycol copolymers. These surfactants are prepared by adding poly(lower)alkylenoxy chains to the free hydroxyl groups of dimethylpolysiloxanols and are available from the Dow Coming Corp as Dow Coming 190 and 193 surfactants (CTFA name: dimethicone copolyol). These surfactants function, with or without any volatile silicones used as solvents, to control foaming produced by the other surfactants, and also impart a shine to metallic, ceramic, and glass surfaces.

Anionic surfactants may also be used in the wetting compositions of the present invention. Anionic surfactants are useful due to their high detergency include anionic detergent salts having alkyl substituents of 8 to 22 carbon atoms such as the water-soluble higher fatty acid alkali metal soaps, e.g., sodium myristate and sodium palmitate. A preferred class of anionic surfactants encompasses the water-soluble sulfated and sulfonated anionic alkali metal and alkaline earth metal detergent salts containing a hydrophobic higher alkyl moiety (typically containing from about 8 to 22 carbon atoms) such as salts of higher alkyl mono or polynuclear aryl sulfonates having from about 1 to 16 carbon atoms in the alkyl group, with examples available as the Bio-Soft series, i.e. Bio-Soft D-40 (Stepan Chemical Co.).

Other useful classes of anionic surfactants include, but are not limited to, the alkali metal salts of alkyl naphthalene sulfonic acids (methyl naphthalene sodium sulfonate, Petro AA, Petrochemical Corporation); sulfated higher fatty acid monoglycerides such as the sodium salt of the sulfated monoglyceride of cocoa oil fatty acids and the potassium salt of the sulfated monoglyceride of tallow fatty acids; alkali metal salts of sulfated fatty alcohols containing from about 10 to 18 carbon atoms (e.g., sodium lauryl sulfate and sodium stearyl sulfate); sodium $C_{14}$–$C_{16}$-alphaolefin sulfonates such as the Bio-Terge series (Stepan Chemical Co.); alkali metal salts of sulfated ethyleneoxy fatty alcohols (the sodium or ammonium sulfates of the condensation products of about 3 moles of ethylene oxide with a $C_{12}$–$C_{15}$ n-alkanol; i.e., the Neodol ethoxysulfates, Shell Chemical Co.); alkali metal salts of higher fatty esters of low molecular weight alkylol sulfonic acids, e.g. fatty acid esters of the sodium salt of isothionic acid, the fatty ethanolamide sulfates; the fatty acid amides of amino alkyl sulfonic acids; e.g., lauric acid amide of taurine; as well as numerous other anionic organic surface active agents such as sodium xylene sulfonate, sodium naphthalene sulfonate, sodium toulene sulfonate and mixtures thereof.

A further useful class of anionic surfactants includes the 8-(4-n-alkyl-2-cyclohexenyl)-octanoic acids, wherein the cyclohexenyl ring is substituted with an additional carboxylic acid group. These compounds or their potassium salts, are commercially-available from Westvaco Corporation as Diacid 1550 or H-240. In general, these anionic surface active agents can be employed in the form of their alkali metal salts, ammonium or alkaline earth metal salts.

Macroemulsions and Microemulsion of Silicone Particles

The wetting composition may further comprise an aqueous microemulsion of silicone particles. For example, U.S. Pat. No. 6,037,407, "Process for the Preparation of Aqueous Emulsions of Silicone Oils and/or Gums and/or Resins" issued Mar. 14, 2000, discloses organopolysiloxanes in an aqueous microemulsion. Desirably, the wetting composition contains less than about 5 weight percent of a microemulsion of silicone particles based on the total weight of the wetting composition. More desirably, the wetting composition contains from about 0.02 weight percent to about 3 weight percent of a microemulsion of silicone particles. Even more desirably, the wetting composition contains from about 0.02 weight percent to about 0.5 weight percent of a microemulsion of silicone particles.

Silicone emulsions in general may be applied to the pre-moistened wipe by any known coating method. For example, the pre-moistened wipe may be moistened with an aqueous composition comprising a water-dispersible or water-miscible, silicone-based component that is compatible with the insolubilizing compound in the wetting composition. Further, the wipe can comprise a nonwoven web of fibers having a water-dispersible binder, wherein the web is moistened with a lotion comprising a silicone-based sulfosuccinate. The silicone-based sulfosuccinate provides gentle and effective cleansing without a high level of surfactant. Additionally, the silicone-based sulfosuccinate provides a solubilization function, which prevents precipitation of oil-soluble components, such as fragrance components, vitamin extracts, plant extracts, and essential oils.

In one embodiment of the present invention, the wetting composition comprises a silicone copolyol sulfosuccinate, such as disodium dimethicone copolyol sulfosuccinate and diammonium dimethicone copolyolsulfosuccinate. Desirably, the wetting composition comprises less than about 2 percent by weight of the silicone-based sulfosuccinate, and more desirably from about 0.05 percent to about 0.30 percent by weight of the silicone-based sulfosuccinate.

In another example of a product comprising a silicone emulsions, Dow Corning 9506 powder may also be present in the wetting composition. Dow Corning 9506 powder is believed to comprise a dimethicone/vinyldimethicone crosspolymer and is a spherical powder, which is said to be useful in controlling skin oils (see "New Chemical Perspectives," *Soap and Cosmetics*, Vol. 76, No. 3, March 2000, p. 12). Thus, a water-dispersible wipe, which delivers a powder effective in controlling skin oil, is also within the, scope of the present invention. Principles for preparing silicone emulsions are disclosed in WO 97/10100, published Mar. 20, 1997.

Emollients

The wetting composition of the present invention may also contain one or more emollients. Suitable emollients include, but are not limited to, PEG 75 lanolin, methyl gluceth 20 benzoate, $C_{12}$–$C_{15}$ alkyl benzoate, ethoxylated cetyl stearyl alcohol, products marketed as Lambent wax WS-L, Lambent WD-F, Cetiol HE (Henkel Corp.), Glucam P20 (Amerchol), Polyox WSR N-10 (Union Carbide), Polyox WSR N-3000 (Union Carbide), Luviquat (BASF), Finsolv SLB 101 (Finetex Corp.), mink oil, allantoin, stearyl alcohol, Estol 1517 (Unichema), and Finsolv SLB 201 (Finetex Corp.).

An emollient can also be applied to a surface of the article prior to or after wetting with the wetting composition. Such an emollient may be insoluble in the wetting composition and can be immobile except when exposed to a force. For example, a petrolatum-based emollient can be applied to one surface in a pattern, after which the other surface is wetted to saturate the wipe. Such a product could provide a cleaning surface and an opposing skin treatment surface.

The emollient composition in such products and other products of the present invention can comprise a plastic or fluid emollient such as one or more liquid hydrocarbons (e.g., petrolatum), mineral oil and the like, vegetable and animal fats (e.g., lanolin, phospholipids and their derivatives) and/or a silicone materials such as one or more alkyl substituted polysiloxane polymers, including the polysiloxane emollients disclosed in U.S. Pat. No. 5,891,126, issued Apr. 6, 1999 to Osborn, III et al. Optionally, a hydrophilic surfactant may be combined with a plastic emollient to improve wettability of the coated surface. In some embodiments of the present invention, it is contemplated that liquid hydrocarbon emollients and/or alkyl substituted polysiloxane polymers may be blended or combined with one or more fatty acid ester emollients derived from fatty acids or fatty alcohols.

In an embodiment of the present invention, the emollient material is in the form of an emollient blend. Desirably, the emollient blend comprises a combination of one or more liquid hydrocarbons (e.g., petrolatum), mineral oil and the like, vegetable and animal fats (e.g., lanolin, phospholipids and their derivatives), with a silicone material such as one or more alkyl substituted polysiloxane polymers. More desirably, the emollient blend comprises a combination of liquid hydrocarbons (e.g., petrolatum) with dimethicone or with dimethicone and other alkyl substituted polysiloxane polymers. In some embodiments of the present invention, it is contemplated that blends of liquid hydrocarbon emollients and/or alkyl substituted polysiloxane polymers may be blended with one or more fatty acid ester emollients derived from fatty acids or fatty alcohols. PEG-7 glyceryl cocoate, available as Standamul HE (Henkel Corp., Hoboken, N.J.), can also be considered.

Water-soluble, self-emulsifying emollient oils, which are useful in the present wetting compositions, include the polyoxyalkoxylated lanolins and the polyoxyalkoxylated fatty alcohols, as disclosed in U.S. Pat. No. 4,690,821, issued Sep. 1, 1987 to Smith et al. The polyoxyalkoxy chains desirably will comprise mixed propylenoxy and ethyleneoxy units. The lanolin derivatives will typically comprise about 20–70 such lower-alkoxy units while the $C_{12}$–$C_{20}$—fatty alcohols will be derivatized with about 8–15 lower-alkyl units. One such useful lanolin derivative is Lanexol AWS (PPG-12-PEG-50, Croda, Inc., New York, N.Y.). A useful poly(15–20)$C_2$–$C_3$-alkoxylate is PPG-5-Ceteth-20, known as Procetyl AWS (Croda, Inc.).

According to one embodiment of the present invention, the emollient material reduces undesirable tactile attributes, if any, of the wetting composition. For example, emollient materials, including dimethicone, can reduce the level of tackiness that may be caused by the ion-sensitive binder or other components in the wetting composition, thus serving as a detackifier.

Desirably, the wetting composition contains less than about 25 weight percent of emollients based on the total weight of the wetting composition. More specifically, the wetting composition may comprise less than about 5 weight percent emollient, and most specifically less than about 2% emollient. More desirably, the wetting composition may contain from about 0.01 weight percent to about 8 weight percent of emollients. Even more desirably, the wetting composition may contain from about 0.2 weight percent to about 2 weight percent of emollients.

In one embodiment, the wetting composition and/or premoistened wipes of the present invention comprise an oil-in-water emulsion comprising an oil phase containing at least one emollient oil and at least one emollient wax stabilizer dispersed in an aqueous phase comprising at least one polyhydric alcohol emollient and at least one organic water-soluble detergent, as disclosed in U.S. Pat. No. 4,559,157, issued Dec. 17, 1985 to Smith et al., the entirety of which is herein incorporated by reference.

Surface Feel Modifiers

Surface feel modifiers are used to improve the tactile sensation (e.g., lubricity) of the skin during use of the product. Suitable surface feel modifiers include, but are not limited to, commercial debonders; and softeners, such as the softeners used in the art of tissue making including quaternary ammonium compounds with fatty acid side groups, silicones, waxes, and the like. Exemplary quaternary ammonium compounds with utility as softeners are disclosed in U.S. Pat. No. 3,554,862, issued to Hervey et al. on Jan. 12, 1971; U.S. Pat. No. 4,144,122, issued to Emanuelsson et al., Mar. 13, 1979, U.S. Pat. No. 5,573,637, issued to Ampulski et al. Nov. 12, 1996; and U.S. Pat. No. 4,476,323, issued to Hellsten et al., Oct. 9, 1984, the entirety of all of which is herein incorporated by reference. Desirably, the wetting composition contains less than about 2 weight percent of surface feel modifiers based on the total weight of the wetting composition. More desirably, the wetting composition contains from about 0.01 weight percent to about 1 weight percent of surface feel modifiers. Even more desirably, the wetting composition contains from about 0.01 weight percent to about 0.05 weight percent of surface feel modifiers.

Fragrances

A variety of fragrances may be used in the wetting composition of the present invention. Desirably, the wetting composition contains less than about 2 weight percent of fragrances based on the total weight of the wetting composition. More desirably, the wetting composition contains from about 0.01 weight percent to about 1 weight percent of fragrances. Even more desirably, the wetting composition contains from about 0.01 weight percent to about 0.05 weight percent of fragrances.

Fragrance Solubilizers

Further, a variety of fragrance solubilizers may be used in the wetting composition of the present invention. Suitable fragrance solubilizers include, but are not limited to, polysorbate 20, propylene glycol, ethanol, isopropanol, diethylene glycol monoethyl ether, dipropylene glycol, diethyl phthalate, triethyl citrate, Ameroxol OE-2 (Amerchol Corp.), Brij 78 and Brij 98 (ICI Surfactants), Arlasolve 200 (ICI Surfactants), Calfax 16L-35 (Pilot Chemical Co.), Capmul POE-S (Abitec Corp.), Finsolv SUBSTANTIAL (Finetex), and the like. Desirably, the wetting composition contains less than about 2 weight percent of fragrance solubilizers based on the total weight of the wetting composition. More desirably, the wetting composition contains from about 0.01 weight percent to about 1 weight percent of fragrance solubilizers. Even more desirably, the wetting composition contains from about 0.01 weight percent to about 0.05 weight percent of fragrance solubilizers.

Opacifiers

Suitable opacifiers include, but are not limited to, titanium dioxide or other minerals or pigments, and synthetic opacifiers, such as REACTOPAQUE® particles (available from Sequa Chemicals, Inc., Chester, S.C.). Desirably, the wetting composition contains less than about 2 weight percent of opacifiers based on the total weight of the wetting composition. More desirably, the wetting composition contains from about 0.01 weight percent to about 1 weight percent of opacifiers. Even more desirably, the wetting composition contains from about 0.01 weight percent to about 0.05 weight percent of opacifiers.

pH Control Agents

Suitable pH control agents for use in the wetting composition of the present invention include, but are not limited to, hydrochloric acid, acetic acid, sodium hydroxide, potassium hydroxide, and the like. An appropriate pH range minimizes the amount of skin irritation resulting from the wetting composition on the skin. Desirably, the pH range of the wetting composition is from about 3.5 to about 6.5. More desirably, the pH range of the wetting composition is from about 4 to about 6. Desirably the overall pH of the wet wipe product; i.e., the complete wet wipe product including the fabric portion and the wetting solution portion, is from about 3.9–4.5; preferably, about 4.2. Desirably, the wetting composition contains less than about 2 weight percent of a pH adjuster based on the total weight of the wetting composition. More desirably, the wetting composition contains from about 0.01 weight percent to about 1 weight percent of a pH adjuster. Even more desirably, the wetting composition contains from about 0.01 weight percent to about 0.05 weight percent of a pH adjuster.

Although a variety of wetting compositions, formed from one or more of the above-described components, may be used with the wet wipes of the present invention, in one embodiment, the wetting composition contains the following components, given in weight percent of the wetting composition, as shown in Table 2 below:

TABLE 2

Wetting Composition Components

| Wetting Composition Component: | Weight Percent: |
|---|---|
| Deionized Water | about 86 to about 98 |
| Insolubilizing compound | about 2 to about 20 |
| Preservative | Up to about 2 |
| Surfactant | Up to about 2 |
| Silicone Emulsion | Up to about 1 |
| Emollient | Up to about 1 |
| Fragrance | Up to about 0.3 |
| Fragrance solubilizer | Up to about 0.5 |
| pH adjuster | Up to about 0.2 |

In another embodiment of the present invention, the wetting composition comprises the following components, given in weight percent of the wetting composition, as shown in Table 3 below:

TABLE 3

Wetting Composition Components

| Class of Wetting Composition Component: | Specific Wetting Composition Component: | Component Name: | Weight Percent: |
|---|---|---|---|
| Vehicle | Deionized Water | | about 86 to about 98 |
| Insolubilizing compound | Sodium Chloride (Millport Ent., Milwaukee, WI) | | about 2 to about 20 |
| Preservative | Glycerin, IPBC and DMDM Hydantoin | Mackstat H-66 (McIntyre Group, Chicago, IL) | Up to about 2 |
| Surfactant | Acyl Glutamate | CS22 (Ajinomoto, Tokyo, Japan) | Up to about 2 |

TABLE 3-continued

Wetting Composition Components

| Class of Wetting Composition Component: | Specific Wetting Composition Component: | Component Name: | Weight Percent: |
|---|---|---|---|
| Silicone Emulsion (Detackifier/Sk in Feel agent) | Dimethiconol and TEA Dodecylbenezene Sulfonate | DC1785 (Dow Corning, Midland, MI) | Up to about 1 |
| Emollient | PEG-75 Lanolin | Solulan L- 575 (Amerchol, Middlesex, NJ) | Up to about 1 |
| Fragrance | Fragrance | Dragoco 0/708768 (Dragoco, Roseville, MN) | Up to about 0.3 |
| Fragrance solubilizer | Polysorbate 20 | Glennsurf L20 (Glenn Corp., St. Paul, MN) | Up to about 0.5 |
| pH adjuster | Malic Acid to pH 5 (Haarman & Reimer, Tetrboro, NJ) | | Up to about 0.2 |

In another embodiment of the present invention, the wetting composition comprises the following components, given in weight percent of the wetting composition, as shown in Table 4 below:

TABLE 4

An Exemplary Wetting Composition

| Class of Wetting composition Component: | Specific Wetting composition Component: | Component Name: | Weight Percent: |
|---|---|---|---|
| Vehicle | Deionized Water | | about 93 |
| Insolubilizing compound | Zinc Chloride | | about 1 |
| Preservative | Glycerin, IPBC and DMDM Hydantoin | Mackstat H-66 | about 1 |
| Surfactant | Acyl Glutamate | CS22/ECS 22P | about 1 |
| Silicone Emulsion | Dimethiconol and TEA Dodecylbenezene Sulfonate | DC 1784/ DC1785 | about 0.5 |
| Emollient | PEG-75 Lanolin | Solulan L- 575 | about 0.25 |
| Fragrance | Fragrance | Dragoco Fragrance 0/708768 | about 0.05 |
| Fragrance solubilizer | Polysorbate 20 | Glennsurf L20 | about 0.25 |
| pH adjuster | Malic Acid to pH 5 | | about 0.07 |

It should be noted that the above-described wetting compositions of the present invention may be used with any one of the above-described triggerable binder compositions of the present invention. Further, the above-described wetting compositions of the present invention may be used with any other binder composition, including conventional binder compositions, or with any known fibrous or absorbent substrate, whether dispersible or not.

Strength Properties

In one embodiment of the present invention, wet wipes are produced using the above-described wetting composition in Table 3 and an air-laid fibrous material comprising about 80 weight percent of bleached kraft fibers and 20 weight percent of any of the above-described ion-specific binder compositions of the present invention, wherein the weight percentages are based on the total weight of the dry nonwoven fabric. In a further embodiment of the present invention, wet wipes are produced using the above-described wetting composition in Table 2 and an air-laid fibrous material comprising 90 weight percent of softwood fibers and 10 weight percent of an ion-sensitive binder of the present invention. The amount of wetting composition added to the nonwoven fabric, relative to the weight of the dry nonwoven fabric in these embodiments, is desirably about 180 percent to about 240 weight percent.

Desirably, the wet wipes of the present invention possess an in-use wet tensile strength cross deckle wet tensile (CDWT) of at least about 100 g/in, and a tensile strength of less than about 30 g/in after being soaked in water having a concentration of $Ca^{2+}$ and/or $Mg^{2+}$ ions of about 50 ppm for about one hour. More desirably, the wet wipes possess an in-use wet tensile strength of at least about 300 g/in (CDWT), and a tensile strength of less than about 20 g/in after being soaked in water having a concentration of $Ca^{2+}$ and/or $Mg^{2+}$ ions of about 50 ppm for about one hour. In a further embodiment, the wet wipes desirably possess an in-use wet tensile strength of at least about 100 g/in (CDWT), and a tensile strength of less than about 30 g/in after being soaked in water having a concentration of $Ca^{2+}$ and/or $Mg^{2+}$ ions of about 200 ppm for about one hour. Even more desirably, the wet wipes possess an in-use wet tensile strength of at least about 300 g/in (CDWT), and a tensile strength of less than about 20 g/in after being soaked in water having a concentration of $Ca^{2+}$ and/or $Mg^{2+}$ ions of about 200 ppm for about one hour.

Desirably, the wet wipes treated with the binder material of the present invention possess an in-use wet tensile strength of at least 100 g/in for a 1 inch width sample in the cross machine direction when soaked with 10% to 400% by weight wet wipes solution containing more than 2% by weight monovalent ion (NaCl) concentration and a tensile strength of less than about 30 g/in after being soaked in deionized water for about one hour. More desirably, the wet wipes treated with the binder material of the present invention possess an in-use tensile strength of at least 200 g/in for a 1 inch width sample in the cross machine direction when soaked with 10% to 400% by weight wet wipes solution containing more than 2% by weight monovalent ion (NaCl) concentration and a tensile strength of less than about 30 g/in after being soaked in deionized water for about one hour. More desirably, the wet wipes treated with the binder material of the present invention possess an in-use tensile strength of at least 300 g/in for a 1 inch width sample in the cross machine direction when soaked with 10% to 400% by weight wet wipes solution containing more than 2% by weight monovalent ion (NaCl) concentration and a tensile strength of less than about 20 g/in after being soaked in deionized water for about one hour.

Desirably, the wet wipes treated with the binder material of the present invention possess an in-use wet tensile strength of at least 100 g/in for a 1 inch width sample in the cross machine direction when soaked with 10% to 400% by weight wet wipes solution containing more than 0.5% by weight $ZnCl_2$ and a tensile strength of less than about 30 g/in after being soaked in deionized water for about one hour. More desirably, the wet wipes treated with the binder material of the present invention possess an in-use tensile strength of at least 200 g/in for a 1 inch width sample in the cross machine direction when soaked with 10% to 400% by weight wet wipes solution containing more than 0.5% by weight $ZnCl_2$ and a tensile strength of less than about 30 g/in after being soaked in deionized water for about one hour. More desirably, the wet wipes treated with the binder material of the present invention possess an in-use tensile strength of at least 300 g/in for a 1 inch width sample in the cross machine direction when soaked with 10% to 400% by weight wet wipes solution containing more than 0.5% by weight $ZnCl_2$ and a tensile strength of less than about 20 g/in after being soaked in deionized water for about one hour.

Products with high basis weights or wet strengths than flushable wet wipes may have relatively higher wet tensile strength. For example, products, such as pre-moistened towels or hard-surface cleaning wipes, may have basis weights above 70 gsm, such as from 80 gsm to 150 gsm. Such products can have CDWT values of 500 g/in or greater, and after soaking values of about 150 g/in or less, more specifically about 100 g/in or less, and most specifically about 50 g/in or less.

Method of Making Wet Wipes

The pre-moistened wipes of the present invention can be made in several ways. In one embodiment, the triggerable polymer composition is applied to a fibrous substrate as part of an aqueous solution or suspension, wherein subsequent drying is needed to remove the water and promote binding of the fibers. In particular, during drying, the binder migrates to the crossover points of the fibers and becomes activated as a binder in those regions, thus providing acceptable strength to the substrate. For example, the following steps can be applied:

1. Providing an absorbent substrate that is not highly bonded (e.g., an unbonded airlaid, a tissue web, a carded web, fluff pulp, etc.).

2. Applying a triggerable polymer composition to the substrate, typically in the form of a liquid, suspension, or foam.

3. Drying the substrate to promote bonding of the substrate. The substrate may be dried such that the peak substrate temperature does not exceed about 100° to 220° C. In one embodiment, the substrate temperature does not exceed 60° C. to 80° C.

5. Applying a wetting composition to the substrate.

6. Placing the wetted substrate in roll form or in a stack and packaging the product.

Application of the triggerable polymer composition to the substrate can be by means of spray; by foam application; by immersion in a bath; by curtain coating; by coating and metering with a wire-wound rod; by passage of the substrate through a flooded nip; by contact with a pre-metered wetted roll coated with the binder solution; by pressing the substrate against a deformable carrier containing the triggerable polymer composition such as a sponge or felt to effect transfer into the substrate; by printing such as gravure, inkjet, or flexographic printing; and any other means known in the art.

In the use of foams to apply a binder or co-binder polymer, the mixture is frothed, typically with a foaming agent, and spread uniformly on the substrate, after which vacuum is applied to pull the froth through the substrate. Any known foam application method can be used, including that of U.S. Pat. No. 4,018,647, "Process for the Impregnation of a Wet Fiber Web with a Heat Sensitized Foamed Latex Binder," issued Apr. 19, 1977 to Wietsma, the entirety of which is herein incorporated by reference. Wietsma discloses a method wherein a foamed latex is heat-sensitized by the addition of a heat-sensitizer such as functional siloxane compounds including siloxane oxyalkylene block copolymers and organopolysiloxanes. Specific examples of applicable heat-sensitizers and their use thereof for the heat sensitization of latices are described in the U.S. Pat. Nos. 3,255,140; 3,255,141; 3,483,240 and 3,484,394, all of which are incorporated herein by reference. The use of a heat-sensitizer is said to result in a product having a very soft and textile-like hand compared to prior methods of applying foamed latex binders.

The amount of heat-sensitizer to be added is dependent on, inter alia, the type of latex used, the desired coagulation temperature, the machine speed and the temperatures in the drying section of the machine, and will generally be in the range of about 0.05 to about 3% by weight, calculated as dry matter on the dry weight of the latex; but also larger or smaller amounts may be used. The heat sensitizer can be added in such an amount that the latex will coagulate far below the boiling point of water, for instance at a temperature in the range of 35° C. to 95° C., or from about 35° C. to 65° C.

Without wishing to be bound by theory, it is believed that a drying step after application of the triggerable binder solution and before application of the wetting composition enhances bonding of a fibrous substrate by driving the binder to fiber crossover points as moisture is driven off, thus promoting efficient use of the binder. However, in an alternative method, the drying step listed above is skipped, and the triggerable polymer composition is applied to the substrate followed by application of the wetting composition without significant intermediate drying. In one version of this method, the triggerable polymer composition selectively adheres to the fibers, permitting excess water to be removed in an optional pressing step without a significant loss of the binder from the substrate. In another version, no significant water removal occurs prior to application of the wetting composition. In yet another alternative method, the triggerable polymer composition and the wetting composition are applied simultaneously, optionally with subsequent addition of salt or other insolubilizing compounds to further render the binder insoluble.

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

As used herein, the "thickness" of a web is measured with a 3-in acrylic plastic disk connected to the spindle of a Mitutoyo Digimatic Indicator (Mitutoyo Corporation, 31–19, Shiba 5-chome, Minato-ku, Tokyo 108, Japan) and which delivers a net load of 0.05 psi to the sample being measured. The Mitutoyo Digimatic Indicator is zeroed when the disk rests on a flat surface. When a sample having a size at least as great as the acrylic disk is placed under the disk, a thickness reading can be obtained from the digital readout of the indicator. Water-dispersible substrates of the present invention can have any suitable thickness, such as from about 0.1 mm to 5 mm. For wet wipes, thicknesses can be in the range of 0.2 mm to about 1 mm, more specifically from about 0.3 mm to about 0.7 mm. Thickness can be controlled, for example, by the application of compaction rolls during or after web formation, by pressing after binder or wetting composition has been applied, or by controlling the tension of winding when forming a roll good.

The use of the platen method to measure thickness gives an average thickness at the macroscopic level. Local thickness may vary, especially if the product has been embossed or has otherwise been given a three-dimensional texture.

EXAMPLE 1

Polymers were synthesized by free radical polymerization of varying combinations of the following monomers: acrylic acid, acrylamide, butyl acrylate, 2-ethylhexyl acrylate and [2(methacryloyloxy)ethyl] trimethyl ammonium chloride ("MQUAT"). Each polymerization was conducted in methanol. A typical procedure is stated below.

Acrylamide (39.1 g, 0.55 mol), butyl acrylate (32.0 g, 0.25 mol), 2-ethylhexyl acrylate (18.4 g, 0.10 mol), and MQUAT (27.6 g of 75 wt % solution, 0.10 mol) were dissolved in 50 g of methanol. A free radical initiator, 2,2"Azobisisobutyronitrile ("AIBN") (0.66 g, 4.0×10' mol) was dissolved in 20 ml of methanol. The monomer solution was deoxygenated by bubbling $N_2$ through the solution for 20 minutes. To a 1000 ml round bottom, three neck flask equipped with a condenser, two addition funnels and a magnetic stirrer was added 125 g of methanol. The solvent was heated to gentle reflux under nitrogen. Monomers and initiator were added simultaneously from the addition funnels over a period of two hours. Polymerization was allowed to proceed for an additional two hours, at the end of which the addition funnels and condenser were replaced with a distillation head and a mechanical stir rod to remove methanol. A steady stream of $N_2$ was maintained during distillation. When the distillation was completed (about 3 hours), 400 g of deionized water was added to the polymer solution. The heat was removed and the solution was allowed to stir overnight.

Alternatively, the polymers can be made by adding the monomers and initiator to the reaction flask all at once and reacting for four hours. This synthesis method is referred as "one pot" synthesis in the subsequent section. A total of eight polymers were synthesized and their compositions are summarized in Table 5 below.

TABLE 5

| | Polymer Composition | | | | |
|---|---|---|---|---|---|
| Sample | % MQUAT | % AM | % AA | % BA | % EHA |
| 1 | 10 | 0 | 55 | 25 | 10 |
| 2 | 10 | 55 | 0 | 25 | 10 |
| 3 | 60 | 0 | 0 | 20 | 20 |
| 4 | 45 | 0 | 0 | 35 | 20 |
| 5 | 35 | 0 | 0 | 35 | 30 |
| 6 | 30 | 0 | 0 | 35 | 35 |
| 7 | 20 | 0 | 0 | 40 | 40 |
| 8 | 15 | 0 | 0 | 45 | 40 |

Sample Preparation

A water-dispersible, wet-laid nonwoven composed of BFF rayon fibers (1.5 d×25 mm) was utilized as the base sheet for testing. Each base sheet was cut to an approximate size of 5.5 in (CD)×9 in (MD). A piece of release paper was placed onto a notepad, followed by a base sheet. Both pieces were taped to the notepad with a single piece of Scotch tape. A #20 grooved, wire-wound rod was laid across the top of the sample. A strip of the polymer solution to be tested was poured along the rod. The rod was then rolled down the length of the sample, with gentle pressure applied. Excess polymer was wiped off the bottom of the release paper, and the sample was placed into a forced air oven at 60° C. for at least 10 minutes. The rod was cleaned between each sample as necessary. Once the samples were dry, they were removed from the oven. The top part of each sample was removed with a paper cutter. Each sample was then peeled from the release paper and the excess polymer film was gently pulled from the edges of the sample. Each sample sheet was then cut into ten 1 in (CD)×4 in (MD) strips.

Tensile Testing

The SinTech 1/D tensile tester with Testworks 3.03 version software was utilized for all sample testing. All testing was conducted in the machine direction using a 50 pound load cell and pneumatic, rubberized grips. The gage length was set at 3 in, and the crosshead speed was 12 in/min. The wet samples were secured in the grips and stretched to failure. The peak load of each sample was recorded as the data of interest. The data was not normalized to a 100% add-on level. A value of "0" was entered for the peak load if the sample was determined to be dispersed. Samples were considered dispersed if individual strips could not be removed from the salt solution intact due to lack of structural integrity.

The in-use strength of each sample was simulated by soaking the tensile samples in various salt solutions. The concentrations of the salt solutions were chosen based upon a 2 wt % NaCl solution, which is equivalent to 0.34 M. The 0.68 M and 1.36 M NaCl solutions correspond to 4 wt % and 8 wt %, respectively. The same molarities were chosen for each of the other salts tested, though the weight percents are not necessarily equivalent to the sodium chloride solutions. Salt solutions tested included 0.34 M NaCl, 0.68 M NaCl, 1.36 M NaCl, 0.34 M $CaCl_2$, 0.68 M $CaCl_2$, 1.36 M $CaCl_2$, 0.34 M $Na_2SO_4$, 0.68 M $Na_2SO_4$, 1.36 M $Na_2SO_4$, 0.17 M $ZnCl_2$, 0.34 M $ZnCl_2$, 0.51 M $ZnCl_2$, 0.34 M $ZnSO_4$, 0.17 M $ZnCl_2$+0.17 M NaCl, 0.34 M LiCl, 0.34 M KCl, 0.34 M $Na_3PO_4$, and 0.34 M$MgCl_2$.

Twenty-four tensile samples were placed into the salt solution to be tested and allowed to soak overnight. Strips were added to the salt solution one at a time in order to avoid sticking the samples together. Average soaking time was approximately 17 hours, and volume of soaking solution was held constant at approximately 500 mL. Following the overnight soak, eight samples were tested directly to determine the peak load. This test simulated storage and in-use strength. Eight samples were placed into 200 ppm $Ca^{2+}$/$Mg^{2+}$ for 1 hour, and eight samples were placed into 200 ppm $Ca^{2+}$/$Mg^{2+}$ for 3 hours. The peak load of the samples was measured following the soaking times. This test simulated disposal in the hardest water found in the United States.

Trigger Property

Polymer 1 showed salt sensitivity and significant strength in several solutions of sodium chloride. However, the polymer failed to disperse in 200 ppm $Ca^{2+}$/$Mg^{2+}$, as shown in Table 6 below.

TABLE 6

Tensile strength of acrylic acid based polymer (g/in)

| Salt Concentration | Overnight soak | 1 hr. in hard water | 3 hr. in hard water |
|---|---|---|---|
| 0.34 M | 565 | 606 | 648 |
| 0.68 M | 639 | 649 | 634 |
| 1.36 M | 722 | 600 | 608 |

It is suspected that the positive charge on the polymer promotes dissociation of carboxylic acid groups creating carboxylate anions. Complex formation between the carboxylate anion and $Ca^{2+}$ leads to cross-linking, which prevents dispersion in hard water. In order to obtain hard water dispersibility, the acrylic acid was replaced with acrylamide, a water-soluble monomer. The acrylamide polymer (sample 2) showed trigger behavior in several salt solutions as summarized in Table 7 below.

TABLE 7

Tensile strength of acrylamide based polymer in various salt solutions (g/in)

| Salt Solution | Overnight Soak | 1 hr. in Hard Water | 3 hr. in Hard Water |
|---|---|---|---|
| 0.34 M NaCl | 311 | 0 | 0 |
| 0.68 M NaCl | 317 | 0 | 0 |
| 1.36 M NaCl | 429 | 0 | 0 |
| 0.34 M CaCl2 | 664 | 636 | 656 |
| 0.68 M CaCl2 | 635 | 662 | 666 |
| 1.36 M CaCl2 | 603 | 616 | 596 |
| 0.34 M Na2SO4 | 289 | 0 | 0 |
| 0.68 M Na2SO4 | 486 | 160 | 0 |
| 1.36 M Na2SO4 | 897 | 265 | 181 |
| 0.17 M ZnC12 | 345 | 0 | 0 |
| 0.34 M ZnZ12 | 519 | 0 | 0 |
| 1.36 M ZnC12 | 661 | 0 | 0 |

General trends showed that increasing the concentration of the salt solution increased the in-use strength of the polymer binder. The performance of the polymer is salt-specific. The polymer showed moderate strength and good dispersibility in NaCl. The strength of the polymer increased almost linearly with increasing $Na_2SO_4$ concentration, but reached good strength only at higher salt level. The dispersibility went in the opposite direction. The polymer showed nice strength in $ZnCl_2$ and good dispersibility. For $CaCl_2$, the polymer showed good strength, independent of salt concentration in the range of investigation, but no strength loss was observed when placed in hard water. Both results suggested the cross-linking of the polymer caused by $Ca^{2+}$. Acrylamide has been generally regarded as salt insensitive, and its interaction with $Ca^{2+}$ is unknown. Based on the fact that the polymer dispersed well in hard water when soaked in other salts, such as $ZnCl_2$ and NaCl, it is clear that retardation only occurs above certain $Ca^{2+}$ concentrations.

One concern with acrylamide based polymer is the toxicity of the residual acrylamide monomer in the polymer solution. To avoid the safety concern, acrylamide was removed from the composition. Sample 3–8 were made with only three monomers: MQUAT, BA and EHA. Table 8 summarized their trigger behavior.

TABLE 8

Soluble properties of polymers of MQUAT, BA and EHA

| Sample | 3 | 4 | 5 | 6 | 7 | 8 |
|---|---|---|---|---|---|---|
| Solubility | soluble | soluble | dispersed | dispersed | triggered | insoluble |

They differ greatly in the salt sensitivity as small changes in composition can have large effects on the behavior of the polymer in solution. In general, their solubility decreases with decreasing MQUAT content. Samples 3 and 4 were soluble in water even in very high salt concentrations. Samples 5 and 6 were soluble in water and precipitated at high salt level, but showed no strength. Sample 8 is insoluble in water due to high hydrophobicity. Sample 7 had the best trigger property for its delicate balance between the hydrophobic and hydrophilic monomers. The behavior of the polymer in various salt solutions is shown in Table 9 below.

TABLE 9

Performance of polymer 7 in various salt solutions (g/in)

| Salt Solution | Overnight Soak in Salt Solution | 1 hr. Soak in Hard Water | 3 hr. Soak in Hard Water |
|---|---|---|---|
| 0.34 M LiCl | 65 | 0 | 0 |
| 0.34 M NaCl | 66 | 0 | 0 |
| 0.34 M KCl | 81 | 0 | 0 |
| 0.34 M $MgCl_2$ | 96 | 0 | 0 |
| 0.34 M $CaCl_2$ | 183 | 0 | 0 |
| 0.34 M $ZnCl_2$ | 861 | 33 | 25 |
| 0.17 M $ZnCl_2$ + 0.17 M NaCl | 819 | 27 | 12 |
| 0.065 M $ZnCl_2$ + 0.15 M NaCl | 370 | 0 | 0 |
| 0.34 M $Na_2SO_4$ | 0 | 0 | 0 |
| 0.34 M $Na_3PO_4$ | 895 | 736 | 699 |

The polymer displayed trigger property in monovalent salts, namely LiCl, NaCl and KCl, but it lacked any significant strength, falling far short of the minimum goal of 300 g/in for in-use strength. The performance in divalent cations was highly selective. The polymer showed unremarkable strength in $MgCl_2$ and $CaCl_2$, but displayed excellent strength of over 800 g/in in $ZnCl_2$. The polymer also had excellent triggerability in mixed salt of 0.1 7M $ZnCl_2$ and 0.17 M NaCl. When the $ZnCl_2$ concentration was reduced to 0.065M, the strength was reduced. The polymer showed good hard water dispersibility from all those salts.

The effect of anions, especially multivalent anions, on the trigger property was tested. The strength of the polymer in NaCl is unremarkable, though the dispersibility is good. The polymer possessed zero strength in $Na_2SO_4$. Following this discovery, the polymer was also tested in $ZnSO_4$, in order to compare the exceptional strength of the polymer in $Zn^{2+}$ ion to its complete lack of strength in $SO_4^{2-}$ ions. The polymer displayed zero strength in $ZnSO_4$ solution. The polymer forms a non-dispersible complex with phosphate ions, as it would not even disperse after several hours in deionized water. Fortunately, phosphate ion is extremely rare in waste water streams, and thus should pose no problem for the dispersibility of the polymer once in a product application.

The "one pot" polymer, which contains 20% MQUAT, 40% BA and 40% EHA, displayed excellent strength of 896.6 g/in following the overnight soak. However, the dispersibility of the "one pot" polymer was not as good as that of the model polymer, as it still displayed 138.7 g/in of strength after one hour in hard water, and 90.2 g/in of strength after a three hour soak. Overall, the "one pot" polymer displays good trigger property. Although the result using the "one pot" were below the desired results, it is believed that a "one pot" polymer having acceptable strength properties can be made by optimization of the polymer design and is therefore considered within the scope of the present invention.

EXAMPLE 2

Polymerization:

Polymers were synthesized by free radical polymerization in the same manner as described above. MQUAT, n-butyl acrylate (BA), and 2-ethylhexyl acrylate (EHA) were utilized in ratios indicated in Table 10.

Polymer composition was characterized by $^{13}$C NMR and the compositions for each sample appear in Table 11. In most cases the polymer compositions agree with the feed ratios within a few percentage points. This would be expected for a homogeneous solution polymerization where all the monomers have a similar reactivity.

TABLE 10

Polymer Feed Ratios

| Sample | NB # | mole % Feed MQUAT | mole % Feed BA | mole % Feed EHA |
|---|---|---|---|---|
| #1 (028) | 7421-028 | 20.0 | 40.0 | 40.0 |
| #2 (041) | 7421-041 | 15.8 | 42.1 | 42.1 |
| #3 (046) | 7421-045 | 243 | 43.2 | 32.4 |
| #4 (064) | 7421-064 | 21.7 | 39.1 | 39.1 |
| #5 (075) | 7421-075 | 12.6 | 58.9 | 28.5 |
| #6 (083) | 7421-083 | 20.0 | 80.0 | 0.0 |
| #7 (094) | 7421-094 | 17.9 | 41.1 | 41.0 |
| #8 (100) | 7421-100 | 14.5 | 42.8 | 42.7 |
| #9 (130) | 7421-130 | 27.3 | 30.4 | 36.3 |

TABLE 11

Polymer Composition

| Sample | mole % MQUAT Found | mole % BA Found | mole % EHA Found |
|---|---|---|---|
| #1 (028) | 19.5 | 43.4 | 37.1 |
| #2 (041) | 18.1 | 46.4 | 35.5 |
| #3 (045) | 25.7 | 43.3 | 31.0 |
| #4 (064) | 22.8 | 403 | 36.8 |
| #5 (075) | 12.1 | 59.4 | 28.5 |
| #6 (083) | 20.2 | 79.8 | 0.0 |
| #7 (094) | 18.3 | 46.2 | 35.5 |
| #8 (100) | 13.3 | 47.6 | 39.1 |
| #9 (130) | 25.6 | 40.5 | 33.9 |

Sample Preparation

Two base sheet materials were utilized to evaluate the cationic binders. The first was a water-dispersible, wet-laid non-woven composed of BFF rayon fibers (1.5 d×25 mm). Each base sheet was cut to an approximate size of 5.5 in (CD)×9 in (MD). A piece of release paper was placed onto a notepad, followed by a base sheet. Both pieces were taped to the notepad with a single piece of Scotch tape. A #20 grooved, wire-wound rod was laid across the top of the sample. A strip of the polymer solution to be tested was poured along the rod. With gentle pressure applied, the rod was then rolled down the length of the sample. Excess polymer was wiped off the bottom of the release paper, and the sample was placed into a forced air oven at 60° C. for at least 10 minutes. The rod was cleaned between each sample as necessary.

Once the samples were dry, they were removed from the oven. The top part of each sample was removed with a paper cutter. Each sample was then peeled from the release paper and the excess polymer fill was gently pulled from the edges of the sample. Each sample sheet was then cut into ten 1 in (CD)×4 in (MD) strips. Add-on for these samples was in the range of 100%.

The second material used was an uncreped through-air dried (UCTAD) tissue basesheet made in the following fashion. A single ply, blended, uncreped through-air dried tissue basesheet was made generally in accordance with U.S. Pat. No. 5,607,551 issued Mar. 4, 1997 to Farrington et al.(the disclosure of which is incorporated herein by reference). More specifically, 65 pounds (oven dry basis) of eucalyptus hardwood Kraft fiber and 35 pounds (oven dried basis) of Northern Softwood Kraft (NSWK) fiber were dispersed in a pulper for 25 minutes at a consistency of 3% and refined before being transferred to a machine chest and diluted to a consistency of 1%. Prior to forming, the stock was further diluted to approximately 0.1% consistency and transferred to a single layer headbox in such a manner as to provide a blended sheet comprising 65% Eucalyptus and 35% NSWK. The formed web was non-compressively dewatered and rush transferred to a transfer fabric traveling at a speed about 25 percent slower than the forming fabric. The web was then transferred to a through drying fabric and dried. The total basis weight of the resulting sheet was 18.5 pounds per 2880 ft$^2$.

The binders were applied via spraying from a pressurized chamber and dried in a through-air drying oven at 165° C. for 2 min. Approximate binder add-on was 20% for all UCTAD samples. Samples were then cut as noted above.

Tensile Testing

The SinTech 1/D tensile tester with Testworks 3.03 version software was utilized for all sample testing. The testing was conducted using the 60 pound load cell and pneumatic, rubberized grips. The gage length was set at 2 in, and the crosshead speed was 12 in/min. The wet samples were secured in the grips and stretched to failure. The peak load of each sample was recorded as the data of interest. A value of "0" was entered for the peak load if the sample was determined to be dispersed. Samples were considered dispersed if individual strips could not be removed from the salt solution intact due to lack of structural integrity.

The in-use strength of each sample was simulated by soaking the tensile samples in various salt solutions noted below. Disposal strength or dispersibility was assessed by transferring samples soaked for a minimum of 12 hours in the salt solutions into deionized water or a hard water simulant (200 ppm $Ca^{2+}/Mg^{2+}$). NaCl (4%) was utilized as well as several divalent metal salts were employed. $ZnCl_2$ at various levels was employed as well as $MgCl_2$, $CaCl_2$, $ZnSO_4$, and $MgSO_4$. Unless otherwise noted, the testing methods were the same as disclosed in Example 1.

Trigger Properties

Data demonstrating the trigger properties for the co- and terpolymers in this study are shown in Tables 12 through 20. Tables 12 and 13 show the cross-deckle wet tensile (Peak Load in g/inch), CDWT, in concentrated NaCl and $ZnCl_2$ solutions. The order of the samples has been rearranged to list them in order of increasing hydrophilicity.

TABLE 12

Wet Tensile Values (g/in.,) for NaCl Wetting Solutions (BFF Rayon)

| Sample | % MQUAT | 5.2% NaCl | 4% NaCl | DI water | Hard water |
|---|---|---|---|---|---|
| #5 (075) | 12.1 | | 826.5 | 494.3 | 572.2 |
| #8 (100) | 13.3 | | 1238.6 | 844.6 | 908.0 |
| #2 (041) | 18.1 | | 241.1 | 158.7 | 114.5 |
| #7 (094) | 18.3 | | 736.9 | 28.0 | 173.1 |
| #1 (028) | 19.5 | | 174.3 | 14.4 | 12.1 |
| #6 (083) | 20.2 | 60.8 | 56.2 | 2.4 | 0.0 |
| #4 (064) | 22.8 | 28.2 | 41.1 | 0.9 | 1.9 |
| #9 (130) | 25.6 | | 9.1 | 0.0 | 0.0 |
| #3 (045) | 25.1 | | 7.4 | 0.0 | 0.0 |

The trigger behavior in NaCl indicates a relatively narrow range of useful compositions At level of 18% MQUAT and below, the binders show good web strength, but fail to re-disperse in DI water or hard water. At moderate incorporation of the MQUAT monomer (~19–22%), some useful web strength is indicated in 4% NaCl. The rayon webs subsequently loose virtually all of their strength in DI and hard water. At relatively high incorporation of MQUAT (>25%), the web strength is below target values in 4% NaCl. The optimum trigger composition appears to contain approximately 20% MQUAT. Note that Sample #6 is a 20/80 MQUAT/BA copolymer, while Sample #1 has a roughly equivalent amounts of BA and EHA.

TABLE 13

Wet Tensile Values (g/in.) for 4% $ZnCl_2$ Wetting Solutions (BFF Rayon)

| Sample | % MQUAT | 4% $ZnCl_2$ | DI water | Hard water |
|---|---|---|---|---|
| #5 (075) | 12.1 | 1019.2 | 445.5 | 403.5 |
| #8 (100) | 13.3 | 1189.9 | 1180.2 | 658.1 |
| #2 (041) | 18.1. | 546.6 | 110.4 | 85.1 |
| #7 (094) | 18.3 | 1107.8 | 159.6 | 658.1 |
| #1 (028) | 19.5 | 743.3 | 26.5 | 29.2 |
| #6 (083) | 20.2 | 679.1 | 4.2 | 0.3 |
| #4 (064) | 22.8 | 981.2 | 5.0 | 4.9 |
| #9 (130) | 25.6 | 726.7 | 9.2 | 8.9 |
| #3 (045) | 25.7 | 776.4 | 1.5 | 0.0 |

A much broader range of useful trigger compositions is evident for samples in a 4% $ZnCl_2$ solution. Samples containing ~19 to 26% MQUAT exhibit very good web strength in the salt solution, but completely loose strength when transferred to DI water or hard water. Binders with approximately 18% or less MQUAT still fail to disperse when transferred to deionized water (DI) water or hard water. One explanation for the differing behavior in NaCl and $ZnCl_2$ is ionic strength. The ionic strength (I) value for 4% $ZnCl_2$ is 0.88, as opposed to an I value of 0.68 for 4% NaCl. The divalent $Zn^{2+}$ ion has a larger effect on ionic strength, and, thus, the two values are not equivalent at identical weight percent.

It can be demonstrated, however, that ionic strength effects alone cannot account for the difference in observed behavior. Table 12 shows wet tensile values for Samples #4 and #6 in 5.2% NaCl (I=0.89), which has an almost identical I as 4% $ZnCl_2$. The binders still fail to develop useful strength properties even in 5.2% NaCl. In fact, the wet tensile values in 4% $ZnCl_2$ are still significantly higher.

To more systematically examine the effect of $ZnCl_2$ on the properties of the binders, a study using 4, 3. 2, and 1% of the salt was performed. These data appear in Tables 14–17 below. At 4% and 3% $ZnCl_2$, Samples 1, 6, 4, 9, and 3 exhibit good trigger properties. Sample #7 exhibits good web strength, but fails to dispersed completely in DI and hard water. Samples 2, 8, and 5 are too hydrophobic to exhibit trigger properties. At 2% $ZnCl_2$, only Sample #1 exhibits good web strength and dispersibility. More hydrophilic samples fail to show sufficient web strength, while more hydrophobic ones do not fully disperse.

TABLE 14

Repeat of Wet Tensile Values (g/in.) for 4% $ZnCl_2$ Wetting Solutions (BFF Rayon).

| Sample | 4% $ZnCl_2$ | DI water | Hard water |
|---|---|---|---|
| #5 (075) | 658.2 | 252.5 | 255.2 |
| #8 (100) | 709.9 | 337.5 | 352.2 |

TABLE 14-continued

Repeat of Wet Tensile Values (g/in.) for 4% $ZnCl_2$
Wetting Solutions (BFF Rayon).

| Sample | 4% $ZnCl_2$ | DI water | Hard water |
|---|---|---|---|
| #2 (041) | n/a | n/a | n/a |
| #7 (094) | 675.1 | 50.9 | 70.4 |
| #1 (028) | 622.0 | 18.2 | 19.2 |
| #6 (083) | 561.6 | 3.3 | 2.4 |
| #4 (064) | 512.4 | 8.1 | 15.9 |
| #9 (130) | 574.1 | 0.0 | 0.0 |
| #3 (046) | 590.2 | 5.5 | 8.8 |

TABLE 15

Wet Tensile Values (g/in.) for 3% $ZnCl_2$
Wetting Solutions (BFF Rayon).

| Sample | 3% $ZnCl_2$ | DI water | Hard water |
|---|---|---|---|
| #5 (075) | 729.1 | 268.4 | 281.5 |
| #8 (1100) | 671.3 | 281.7 | 318.7 |
| #2 (041) | n/a | n/a | n/a |
| #7 (094) | 676.9 | 43.3 | 63.5 |
| #1 (028) | 535.0 | 6.9 | 13.4 |
| #6 (083) | 324.5 | 0.0 | 0.0 |
| #4 (064) | 516.0 | 4.6 | 10.4 |
| #9 (130) | 288.5 | 0.0 | 0.0 |
| #3 (046) | 497.4 | 2.1 | 7.8 |

In 1% $ZnCl_2$, Sample #1 indicates some trigger property, but the level of strength developed is below preferred levels. Interestingly, at this low level of salt, Sample #7 exhibits some useful trigger properties. The strength is in the low range and the dispersibilty is slightly less than desired, but the effect is clear.

TABLE 16

Wet Tensile Values (g/in.) for 2% $ZnCl_2$
Wetting Solutions (BFF Rayon).

| Sample | 2% $ZnCl_2$ | DI water | Hard water |
|---|---|---|---|
| #5 (075) | 615.9 | 177.9 | 253.3 |
| #8 (100) | 651.6 | 322.9 | 347.6 |
| #2 (041) | n/a | n/a | n/a |
| #7 (094) | 552.0 | 34.5 | 71.5 |
| #1 (028) | 385.8 | 6.0 | 8.9 |
| #6 (083) | 0.0 | 0.0 | 0.0 |
| #4 (064) | 89.9 | 0.0 | 4.5 |
| #9 (130) | 0.0 | 0.0 | 0.0 |
| #3 (045) | 12.4 | 0.0 | 0.0 |

TABLE 17

Wet Tensile Values (g/in.) for 1% $ZnCl_2$
Wetting Solutions (BFF Rayon).

| Sample | 1% $ZnCl_2$ | DI water | Hard water |
|---|---|---|---|
| #5 (075) | 474.09 | 293.02 | 279.90 |
| #8 (100) | 482.82 | 258.83 | 298.85 |
| #2 (041) | n/a | n/a | n/a |
| #7 (094) | 200.91 | 9.36 | 24.90 |
| #1 (028) | 48.42 | 0.00 | 0.00 |
| #6 (083) | 0.00 | 0.00 | 0.00 |
| #4 (064) | 0.00 | 0.00 | 0.00 |
| #9 (130) | 0.00 | 0.00 | 0.00 |
| #3 (045) | 0.00 | 0.00 | 0.00 |

It is apparent that the hydrophobic/hydrophilic balance is very important with these cationic binders, even though the trigger range and level of salt necessary are much broader. To further demonstrate this effect, MQUAT polymers with 0, 50, and 20 mole % BA were synthesized and tested. These data appear in Table 9. The MQUAT homopolymer and the 50/50 BA copolymer fail to show sufficient strength in the web. The 20/80 MQUAT/BA copolymer exhibits good strength and dispersibility in 4% $ZnCl_2$. Clearly, the level of hydrophobe plays a role in the adhesive properties of these binders.

TABLE 18

Effect of BA Co-monomer on Wet Tensile (BFF Rayon).

| Sample | NB# | mole % Feed MQUAT | mole % Feed BA | CDWT (g/in.)$ZnCl_2$ | CDWT (g/in.) DI Water | CDWT (g/in.) Hard Water |
|---|---|---|---|---|---|---|
| #10 | 6787-34 | 20 | 80 | 560.3 | 0 | 0 |
| #12 | 6787-54 | 50 | 50 | 0 | 0 | 0 |
| #11 | 6787-38 | 100 | 0 | 0 | 0 | 0 |

An UCTAD tissue substrate was also examined using ~20% add-on of the 20/80 MQUAT/BA copolymer (#6). CDWT as a function of percent $ZnCl_2$ solution is shown in Table 19. In general, the same trends seen with the rayon basesheets are apparent. However, the dispersibility for 4% and 3% $ZnCl_2$ seems to suffer on the UCTAD basesheet. At 2% $ZnCl_2$, the system actually seems to show a good balance of strength and re-dispersibility. The strength falls below an acceptable level when 1% $ZnCl_2$ is employed.

TABLE 19

Effect of % $ZnCl_2$ on CDWT for
UCTAD tissue using Sample #6

| % $ZnCl_2$ | Salt solution | DI water | Hard water |
|---|---|---|---|
| 4 | 396.7 | n/a | 36.4 |
| 3 | 522.3 | 18.4 | 34 |
| 2 | 296.2 | 2.2 | 11.7 |
| 1 | 55.9 | 0.1 | 0.2 |

The effect of other divalent ions, as well as the effect of different counterions is shown in Table 20. Good strength is apparent in 4% $ZnCl_2$, as noted before. Also, other salts of divalent ions, such as $MgCl_2$ and $CaCl_2$ can provide trigger properties at acceptable strength levels. However, when the sulfate salts of these ions are employed, insufficient strength or trigger properties result. Apparently, the trigger behavior in these systems is mediated by both the cation and the anion of the salt employed.

TABLE 20

Effect of divalent ions and counterions on
CDWT using Sample #6 on UCTAD tissue

| Salt Type | 4% Solution | DI water | Hard water |
|---|---|---|---|
| $ZnCl_2$ | 364.2 | 37.6 | 49.4 |
| $MgCl_2$ | 133.9 | 6.6 | 8.6 |
| $CaCl_2$ | 93.3 | 3.9 | 7.4 |
| $ZnSO_4$ | 9.8 | 7.9 | 13.3 |
| $MgSO_4$ | 15.6 | 8.8 | 15.4 |

These results seem to indicate "ion specific" interactions rather than the "salting-out" effect seen in previous systems. Although ionic strength may play a role here, the data presented here clearly indicates a new type of trigger mechanism based on hydrophobic associations and ion-specific interactions.

EXAMPLE 3

Polymerization:

Cationic triggerable polymers were synthesized by free radical polymerization in the same manner as described above. MQUAT, n-butyl acrylate (BA), and 2-ethylhexyl acrylate (EHA) were utilized in the following ratios: MQUAT 20 mole percent, BA 40 mole percent and EHA 40 mole percent. It is stable in high salt solutions, such as 4 weight percent ZnCl2, and is soluble in water when the salt concentration drops below a certain level, such as 0.5 weight percent. Because of the nature of the charge groups the polymer carries, its dispersibility is virtually unaffected by the presence of divalent cations, such as $Ca^{2+}$ and $Mg^{2+}$ up to 200 ppm, and, therefore, the polymer performs well even in the hardest water found in the United States households.

Wet Wipe Sample Preparation

To make a wet wipe product, the ion-sensitive cationic polymer was applied in an aqueous solution to a substrate by spraying. The substrate was a water-dispersible, wet-laid non-woven composed of BFF rayon fibers (1.5 d×25 mm). Two different binder solution were prepared. The first solution was an aqueous solution of the ion-sensitive polymer. The other solution was an aqueous solution of the ion-sensitive polymer (75 weight percent) and a co-binder (25 weight percent) in the form of an emulsion polymer. The co-binder provides several advantages to the polymer system, including rheology modification for better spray application, better binder penetration for higher strength, tack reduction and cost savings.

Selection of the emulsion system for the co-binder is critical. The emulsion system of the co-binder must not interact with the ion-sensitive cationic polymer such that it interferes with the trigger property. Three emulsion-based polymers were tested. Rovene 4817 a styrene butadiene copolymer manufactured by Mallard Creek Polymers, Charlotte, N.C., and Rhoplex P-376 a styrene acrylate copolymer manufactured by Rohm and Haas, Philadelphia, Pa. The combination of the cationic polymer and the Rovene 4817 and the Rhoplex P-376 caused sever precipitation of the binder from the aqueous solution. It was suspected that the anionic emulsion surfactants used in the Rovene 4817 and the Rhoplex P-376 may have interacted with the cationically charged polymer through electrostatic forces, thus resulting in the precipitation of the binder out of suspension. It was therefore determined that these emulsion polymers were not suitable for use with the cationic ion-sensitive polymer of the present invention.

The third emulsion polymer that was investigated was Duroset RB® manufactured by National Starch and Chemical Company. Duroset RB® is an ethylene vinyl acetate copolymer. When the Duroset RB® was combined with the cationic polymer, only a small amount of precipitation was observed, and did not interfere with the trigger property of the binder system.

Two different samples were prepared. One sample of the substrate included a binder made from only the cationic polymer; the other substrate contained a binder made from 75 weight percent cationic polymer and 25 weight percent Duroset RB®. The samples were prepared in the same manner as disclosed in co-pending U.S. patent application Ser. No. 09/564,939 assigned to Kimberly-Clark (the disclosure of which is incorporated herein by reference).

The samples were soaked in an aqueous solution containing 4 weight percent $ZnCl_2$. The samples were then soaked in water containing 200 ppm $Ca^{2+}/Mg^{2+}$. The samples were then tested for tensile strength. The results of this test are shown in Table 21 below.

TABLE 1

Trigger Performance of Cationic Binder

| Sample | 4% $ZnCl_2$ | 1 hr soak in hard water | 3 hr soak in hard water |
|---|---|---|---|
| 100% Binder | 861 | 33 | 25 |
| 75% Binder/ 25% Duroset RB ® | 714 | 11 | 0 |

The foregoing test results show that the tensile strength was reduced by about 20% with the addition of 25% Duroset RB®. Both samples showed acceptable wet strength in the 4% $ZnCl_2$ solution. After one hour of soaking in 200 ppm $Ca^{2+}/Mg^{2+}$ solution, the peak load decreased significantly. The strength was practically zero. After three hours of soaking, the sample containing the Duroset RB® was fully dispersed without shaking.

It is contemplated that emulsion polymers that use only a small amount of anionic surfactant or use a weak anionic surfactant may be used as the co-binder in the present invention as long as they do not cause precipitation to such an extent that it interferes with the trigger property of the polymer composition. It is also specifically contemplated that other emulsion polymers using nonionic or cationic surfactant systems may also be used as the co-binder in the present invention.

It should be understood, of course, that the foregoing relates only to certain disclosed embodiments of the present invention and that numerous modifications or alterations may be made therein without departing from the spirit and scope of the invention as set forth in the appended claims.

What is claimed is:

1. A polymer formulation comprising a cationic polymer comprising the polymerization product of a mixture comprising cationic monomers and non-cationic monomers and a non-crosslinked co-binder polymer dispersed in the cationic polymer, wherein the cationic polymer is the continuous phase and the non-crosslinked co-binder polymer is the discontinuous phase and wherein the polymer formulation is insoluble in aqueous solution containing at least about 0.5 weight percent divalent metal salt capable of forming complex anions in water in the presence of said cationic polymer and the polymer formulation is dispersible in water containing up to about 200 ppm of one or more mono or multivalent ions.

2. A polymer formulation comprising a cationic polymer comprising the polymerization product of a mixture comprising cationic monomers and water insoluble, hydrophobic monomers and a non-crosslinked co-binder polymer dispersed in the cationic polymer, wherein the cationic polymer is the continuous phase and the non-crosslinked co-binder polymer is the discontinuous phase and wherein the polymer formulation is insoluble in aqueous solution containing at least about 0.5 weight percent divalent metal salt capable of forming complex anions in water in the presence of said cationic polymer and the polymer formulation is dispersible in water containing up to about 200 ppm of one or more mono or multivalent ions.

3. A polymer formulation comprising a cationic polymer and a co-binder dispersed therein, wherein said cationic polymer comprises the polymerization product of a mixture comprising cationic monomers and water insoluble, hydrophobic monomers, wherein the cationic polymer is the continuous phase and the co-binder polymer is the discontinuous phase and wherein the polymer formulation is insoluble in aqueous solution containing at least about 0.5 weight percent divalent metal salt capable of forming complex anions in water in the presence of said cationic polymer and the polymer formulation is dispersible in water containing up to about 200 ppm of one or more mono or multivalent ions.

4. The polymer formulation of claim 1, wherein the cationic polymer comprises the polymerization product of a mixture comprising cationic monomers, water insoluble, hydrophobic monomers and hydrophilic monomers.

5. The polymer formulation of claim 1, wherein the cationic polymer comprises the polymerization product of a mixture comprising cationic monomers, water insoluble, hydrophobic monomers and water-soluble nonionic monomers.

6. The polymer formulation of claim 2, wherein the cationic polymer comprises the polymerization product of a mixture comprising cationic monomers, water insoluble, hydrophobic monomers and hydrophilic monomers or water-soluble nonionic monomers.

7. The polymer formulation of claim 3, wherein the cationic polymer comprises the polymerization product of a mixture comprising cationic monomers, water insoluble, hydrophobic monomers and hydrophilic monomers or water-soluble nonionic monomers.

8. A polymer formulation comprising a cationic polymer comprising the polymerization product of a mixture comprising cationic monomers and non-cationic monomers and a non-crosslinked co-binder polymer dispersed in the cationic polymer, wherein the cationic polymer is the continuous phase and the non-crosslinked co-binder polymer is the discontinuous phase and wherein the polymer formulation is insoluble in aqueous solution containing at least about 0.5 weight percent divalent metal salt and the polymer formulation is dispersible in water containing up to about 200 ppm of one or more mono or multivalent ions.

9. A polymer formulation comprising a cationic polymer comprising the polymerization product of a mixture comprising cationic monomers and water insoluble, hydrophobic monomers and a non-crosslinked co-binder polymer dispersed in the cationic polymer, wherein the cationic polymer is the continuous phase and the non-crosslinked co-binder polymer is the discontinuous phase and wherein the polymer formulation is insoluble in aqueous solution containing at least about 0.5 weight percent divalent metal salt and the polymer formulation is dispersible in water containing up to about 200 ppm of one or more mono or multivalent ions.

10. A polymer formulation comprising a cationic polymer and a co-binder dispersed therein, wherein said cationic polymer comprises the polymerization product of a mixture comprising cationic monomers and water insoluble, hydrophobic monomers, wherein the cationic polymer is the continuous phase and the co-binder polymer is the discontinuous phase and wherein the polymer formulation is insoluble in aqueous solution containing at least about 0.5 weight percent divalent metal salt and the polymer formulation is dispersible in water containing up to about 200 ppm of one or more mono or multivalent ions.

* * * * *